US012773568B2

(12) United States Patent
Urman et al.

(10) Patent No.: US 12,773,568 B2
(45) Date of Patent: Oct. 27, 2026

(54) METHODS, SYSTEMS, AND APPARATUSES FOR OPTIMIZING TRANSDUCER ARRAY PLACEMENT

(71) Applicant: Novocure GmbH, Root (CH)

(72) Inventors: Noa Urman, Haifa (IL); Reuven Ruby Shamir, Haifa (IL); Zeev Bomzon, Haifa (IL); Eduard G. Fedorov, Haifa (IL); Yoram Wasserman, Haifa (IL)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 18/903,245

(22) Filed: Oct. 1, 2024

(65) Prior Publication Data

US 2025/0018210 A1 Jan. 16, 2025

Related U.S. Application Data

(62) Division of application No. 17/109,918, filed on Dec. 2, 2020, now Pat. No. 12,115,381.

(60) Provisional application No. 62/942,595, filed on Dec. 2, 2019.

(51) Int. Cl.

| | |
|---|---|
| ***A61N 1/40*** | (2006.01) |
| ***A61B 34/10*** | (2016.01) |
| ***G16H 20/40*** | (2018.01) |
| ***G16H 50/20*** | (2018.01) |

(52) U.S. Cl.

CPC ................ *A61N 1/40* (2013.01); *A61B 34/10* (2016.02); *G16H 20/40* (2018.01); *G16H 50/20* (2018.01); *A61B 2034/105* (2016.02)

(58) Field of Classification Search

CPC ......................... A61B 2034/105; A61B 34/10; A61N 1/0476; A61N 1/0496; A61N 1/36002; A61N 1/40; A61N 1/403; G16H 20/40; G16H 50/20

See application file for complete search history.

(56) References Cited

U.S. PATENT DOCUMENTS

| | | | |
|---|---|---|---|
| 7,146,210 B2 | 12/2006 | Palti | |
| 7,565,205 B2 | 7/2009 | Palti | |
| 9,833,617 B2 | 12/2017 | Travers et al. | |
| 10,188,851 B2 | 1/2019 | Wenger et al. | |
| 10,675,460 B2 | 6/2020 | Travers et al. | |
| 11,013,909 B2 | 5/2021 | Wenger et al. | |
| 11,154,707 B2 | 10/2021 | Bomzon et al. | |
| D934,892 S | 11/2021 | Hershkovich et al. | |
| 2018/0160933 A1 | 6/2018 | Urman et al. | |
| 2019/0030372 A1 | 1/2019 | Macdonald et al. | |
| 2019/0117956 A1* | 4/2019 | Wenger ................ | A61N 1/0456 |

(Continued)

FOREIGN PATENT DOCUMENTS

| | | |
|---|---|---|
| CN | 109558912 A | 4/2019 |
| CN | 109641130 A | 4/2019 |

(Continued)

OTHER PUBLICATIONS

Ballo, et al., "Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial," International Journal of Radiation Oncology, Biology, Physics, 2019; vol. 104, No. 5, pp. 1106-1113.

(Continued)

*Primary Examiner* — Mark D Remaly

(74) *Attorney, Agent, or Firm* — McCarter & English, LLP; Michael A. Sartori

(57) ABSTRACT

Methods, systems, and apparatuses are described for optimizing placement of transducer arrays on a patient.

20 Claims, 21 Drawing Sheets

(56) References Cited

U.S. PATENT DOCUMENTS

| | | | |
|---|---|---|---|
| 2019/0117963 | A1 | 4/2019 | Travers et al. |
| 2019/0308016 | A1 | 10/2019 | Wenger et al. |
| 2019/0314631 | A1 | 10/2019 | Wong et al. |
| 2020/0114141 | A1 | 4/2020 | Bomzon et al. |
| 2020/0129761 | A1 | 4/2020 | Bomzon et al. |
| 2020/0146586 | A1 | 5/2020 | Naveh et al. |
| 2020/0219261 | A1 | 7/2020 | Shamir et al. |
| 2020/0372705 | A1 | 11/2020 | Hershkovich et al. |
| 2021/0060334 | A1 | 3/2021 | Avraham et al. |
| 2021/0162228 | A1 | 6/2021 | Urman et al. |
| 2021/0187277 | A1 | 6/2021 | Wasserman et al. |
| 2021/0196207 | A1 | 7/2021 | Shamir et al. |
| 2021/0196943 | A1 | 7/2021 | Shamir et al. |
| 2021/0201572 | A1 | 7/2021 | Bomzon |
| 2021/0299439 | A1 | 9/2021 | Shamir et al. |

FOREIGN PATENT DOCUMENTS

| | | | |
|---|---|---|---|
| EP | 0330797 | A3 | 9/1990 |
| GB | 1419660 | A | 12/1975 |
| GB | 2026322 | A | 2/1980 |
| GB | 2043453 | A | 10/1980 |
| JP | 2007-533389 | A | 11/2007 |
| JP | 2019-500179 | A | 1/2019 |
| WO | WO-01/60994 | A1 | 8/2001 |
| WO | WO-2010/120823 | A2 | 10/2010 |
| WO | WO-2011/047387 | A2 | 4/2011 |
| WO | WO-2017/72706 | A1 | 5/2017 |
| WO | WO-2018/057529 | A1 | 3/2018 |
| WO | WO-2018/109691 | A2 | 6/2018 |
| WO | WO-2020/168035 | A1 | 8/2020 |
| WO | WO-2020/225599 | A1 | 11/2020 |

OTHER PUBLICATIONS

Hosny, et al., "Unlocking Vendor-Specific Tags: Three-Dimensional Printing of Echocardiographic Data Sets," The Journal of Thoracic and Cardiovascular Surgery, Jan. 2018, vol. 155, No. 1, pp. 143-145 e1.

Bücking, et al., "From Medical Imaging Data to 3D Printed Anatomical," May 31, 2017, 7 pages, https://doi.org/10.1371/journal.pone.0178540.

* cited by examiner

| Table 3 | | | |
|---|---|---|---|
| **Transducer Array Pair 1** | **Transducer Array Pair 2** | **Dose Metric** | **Angle** |
| 1106A:1106F | 1106B:1106G | Dose Metric 1 | 30 |
| 1106A:1106F | 1106D:1106H | Dose Metric 2 | 90 |
| 1106A:1106F | 1106E:1106I | Dose Metric 3 | 120 |
| 1106B 1106G | 1106D:1106H | Dose Metric 4 | 60 |
| 1106B:1106G | 1106E:1106I | Dose Metric 5 | 90 |
| 1106D:1106H | 1106E:1106I | Dose Metric 6 | 30 |

METHODS, SYSTEMS, AND APPARATUSES FOR OPTIMIZING TRANSDUCER ARRAY PLACEMENT

CROSS-REFERENCE TO RELATED PATENT APPLICATIONS

This application is a divisional application of U.S. patent application Ser. No. 17/109,918, filed Dec. 2, 2020, which claims priority to U.S. Provisional Application No. 62/942,595 filed Dec. 2, 2019, which are herein incorporated by reference in their entirety.

BACKGROUND

Tumor Treating Fields, or TTFields, are low intensity (e.g., 1-3 V/cm) alternating electric fields within the intermediate frequency range (100-300 kHz). This non-invasive treatment targets solid tumors and is described in U.S. Pat. No. 7,565,205, which is incorporated herein by reference in its entirety. TTFields disrupt cell division through physical interactions with key molecules during mitosis. TTFields therapy is an approved mono-treatment for recurrent glioblastoma and an approved combination therapy with chemotherapy for newly diagnosed patients. These electric fields are induced non-invasively by transducer arrays (i.e., arrays of electrodes) placed directly on the patient's scalp. TTFields also appear to be beneficial for treating tumors in other parts of the body.

SUMMARY

Described are methods comprising determining a region-of-interest (ROI) within a 3D model of a portion of a subject's body, determining, based on a center of the ROI, a plane that transverses the portion of the subject's body, wherein the plane comprises a plurality of pairs of positions along a contour of the plane, adjusting, based on an anatomical restriction, one or more positions of the plurality of pairs of positions to generate a modified plane, determining, for each pair of positions of the plurality of pairs positions on the modified plane, a simulated electric field distribution, determining, based on the simulated electric field distributions, a dose metric for each pair of positions of the plurality of pairs positions, determining one or more sets of pairs of positions of the plurality of pairs of positions that satisfy an angular restriction between pairs of transducer arrays, and determining, based on the dose metrics and the one or more sets of pairs of positions that satisfy the angular restriction, one or more candidate transducer array layout maps.

Also described are methods comprising determining a three-dimensional (3D) model of a portion of a subject's body, determining a region-of-interest (ROI) within the 3D model of the portion of the subject's body, determining, for each of a plurality of positions for a pair of transducer arrays, based on the 3D model, the ROI, and an anatomical restriction parameter, an electric field distribution map, determining, for each combination of a plurality of combinations of two pairs of transducer arrays, based on the electric field distribution map, a plurality of dose metrics in the ROI, determining, based on an angular restriction parameter and the plurality of dose metrics in the ROI, one or more candidate transducer array layout plans, determining, for each of the one or more candidate transducer array layout plans, one or more adjusted candidate transducer array layout plans by adjusting a position or an orientation of one or more transducer arrays of the pair of transducer arrays, determining, for each adjusted candidate transducer array layout plan, an adjusted dose metric in the ROI, and determining, based on the adjusted dose metric in the ROI, a final transducer array layout plan from the adjusted candidate transducer array layout plans.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

Figure 1:
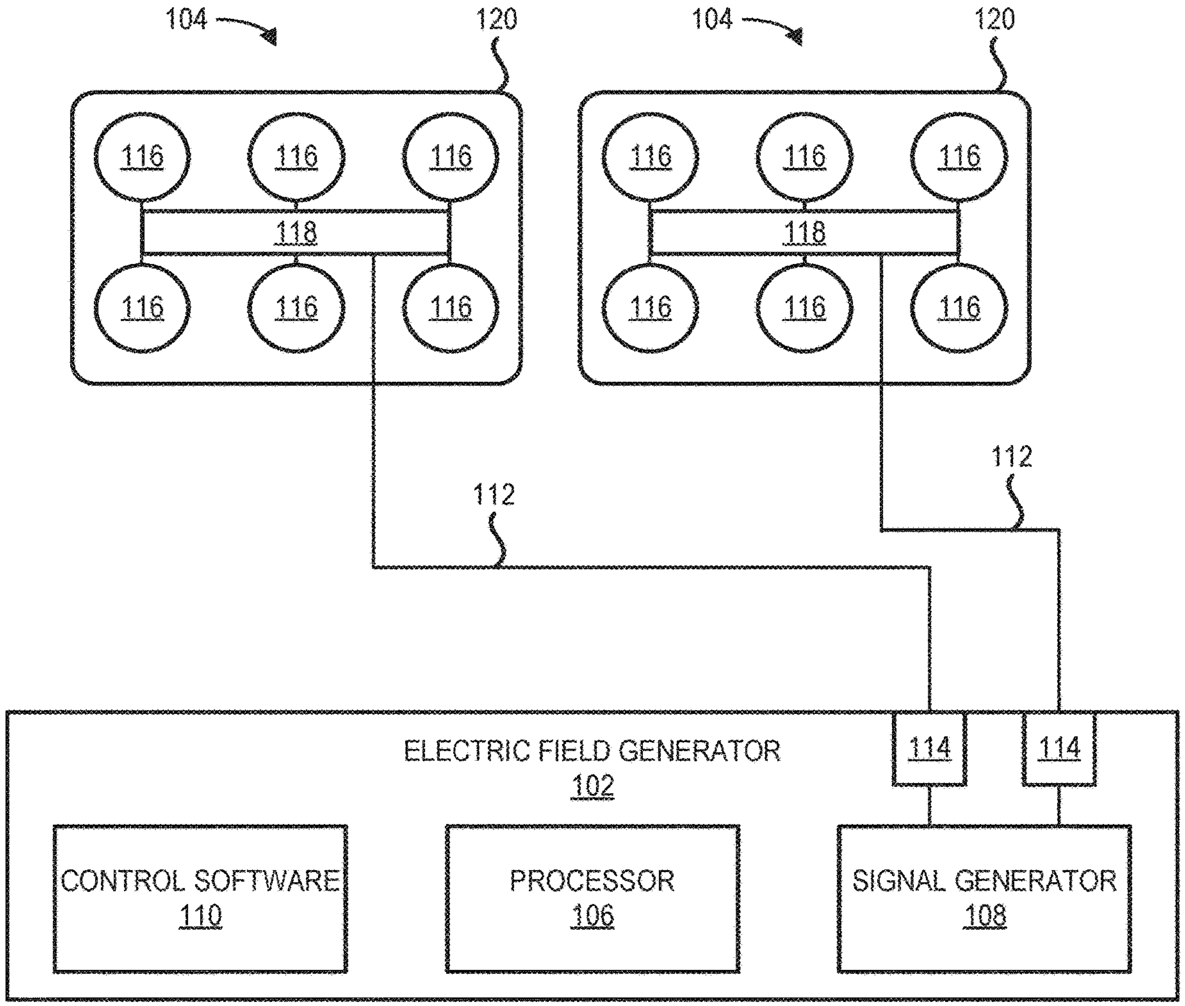
FIG. 1 shows an example apparatus for electrotherapeutic treatment.

Before the present methods and systems are disclosed and described, it is to be understood that the methods and systems are not limited to specific methods, specific components, or to particular implementations. It is also to be understood that the terminology used herein is to describe particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes-from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

TTFields, also referred to herein as alternating electric fields, are established as an anti-mitotic cancer treatment modality because they interfere with proper microtubule assembly during metaphase and eventually destroy the cells during telophase and cytokinesis. The efficacy increases with increasing field strength and the optimal frequency are cancer cell line dependent with 200 kHz being the frequency for which inhibition of glioma cell growth caused by TTFields is highest. For cancer treatment, non-invasive devices were developed with capacitively coupled transducers that are placed directly at the skin region close to the tumor, for example, for patients with Glioblastoma Multiforme (GBM), the most common primary, malignant brain tumor in humans.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, one pair of transducer arrays may be located to the left and right (LR) of the tumor, and the other pair of transducer arrays may be located anterior and posterior (AP) to the tumor. Cycling the field between these two directions (i.e., LR and AP) ensures that a maximal range of cell orientations is targeted. Other positions of transducer arrays are contemplated beyond perpendicular fields. In an embodiment, asymmetric positioning of three transducer arrays is contemplated wherein one pair of the three transducer arrays may deliver alternating electric fields and then another pair of the three transducer arrays may deliver the alternating electric fields, and the remaining pair of the three transducer arrays may deliver the alternating electric fields.

In-vivo and in-vitro studies show that the efficacy of TTFields therapy increases as the intensity of the electric field increases. Therefore, optimizing array placement on the patient's scalp to increase the intensity in the diseased region of the brain is standard practice for the Optune system. Array placement optimization may be performed by “rule of thumb” (e.g., placing the arrays on the scalp as close to the tumor as possible), measurements describing the geometry of the patient's head, tumor dimensions, and/or tumor location. Measurements used as input may be derived from imaging data. Imaging data is intended to include any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electric field distributes within the head as a function of the positions of the array and, in some aspects, take account for variations in the electrical property distributions within the heads of different patients.

FIG. 1 shows an example apparatus 100 for electrotherapeutic treatment. Generally, the apparatus 100 may be a portable, battery or power supply operated device which produces alternating electric fields within the body via non-invasive surface transducer arrays. The apparatus 100 may comprise an electric field generator 102 and one or more transducer arrays 104. The apparatus 100 may be configured to generate tumor treatment fields (TTFields) (e.g., at 150 kHz) via the electric field generator 102 and deliver the TTFields to an area of the body through the one or more transducer arrays 104. The electric field generator 102 may be a battery and/or power supply operated device. In an embodiment, the one or more transducer arrays 104 are uniformly shaped. In an embodiment, the one or more transducer arrays 104 are not uniformly shaped.

The electric field generator 102 may comprise a processor 106 in communication with a signal generator 108. The electric field generator 102 may comprise control software 110 configured for controlling the performance of the processor 106 and the signal generator 108.

The signal generator 108 may generate one or more electric signals in the shape of waveforms or trains of pulses. The signal generator 108 may be configured to generate an alternating voltage waveform at frequencies in the range from about 50 kHz to about 500 kHz (preferably from about 100 kHz to about 300 kHz) (e.g., the TTFields). The voltages are such that the electric field intensity in tissue to be treated is in the range of about 0.1 V/cm to about 10 V/cm.

One or more outputs 114 of the electric field generator 102 may be coupled to one or more conductive leads 112 that are attached at one end thereof to the signal generator 108. The opposite ends of the conductive leads 112 are connected to the one or more transducer arrays 104 that are activated by the electric signals (e.g., waveforms). The conductive leads 112 may comprise standard isolated conductors with a flexible metal shield and may be grounded to prevent the spread of the electric field generated by the conductive leads 112. The one or more outputs 114 may be operated sequentially. Output parameters of the signal generator 108 may comprise, for example, an intensity of the field, a frequency of the waves (e.g., treatment frequency), and a maximum allowable temperature of the one or more transducer arrays 104. The output parameters may be set and/or determined by the control software 110 in conjunction with the processor 106. After determining a desired (e.g., optimal) treatment frequency, the control software 110 may cause the processor 106 to send a control signal to the signal generator 108 that causes the signal generator 108 to output the desired treatment frequency to the one or more transducer arrays 104.

The one or more transducer arrays 104 may be configured in a variety of shapes and positions to generate an electric field of the desired configuration, direction, and intensity at a target volume to focus treatment. The one or more transducer arrays 104 may be configured to deliver two perpendicular field directions through a volume of interest.

The one or more transducer arrays 104 arrays may comprise one or more electrodes 116. The one or more electrodes 116 may be made from any material with a high dielectric constant. The one or more electrodes 116 may comprise, for example, one or more insulated ceramic discs. The electrodes 116 may be biocompatible and coupled to a flexible circuit board 118. The electrodes 116 may be configured to not come into direct contact with the skin as the electrodes 116 are separated from the skin by a layer of conductive hydrogel (not shown) (similar to that found on electrocardiogram pads).

The electrodes 116, the hydrogel, and the flexible circuit board 118 may be attached to a hypoallergenic medical adhesive bandage 120 to keep the one or more transducer arrays 104 in place on the body and in continuous direct contact with the skin. Each transducer array 104 may comprise one or more thermistors (not shown), for example, 8 thermistors, (accuracy ±1° C.) to measure skin temperature beneath the transducer arrays 104. The thermistors may be configured to measure skin temperature periodically, for example, every second. The thermistors may be read by the control software 110 while the TTFields are not being delivered to avoid any interference with the temperature measurements.

If the temperature measured is below a pre-set maximum temperature (Tmax), for example, 38.5-40.0° C.±0.3° C., between two subsequent measures, the control software 110 can increase current until the current reaches maximal treatment current (for example, 4 Amps peak-to-peak). If the temperature reaches Tmax+0.3° C. and continues to rise, the control software 110 can lower the current. If the temperature rises to 41° C., the control software 110 can shut off the TTFields therapy and an overheating alarm can be triggered.

Figure 2:
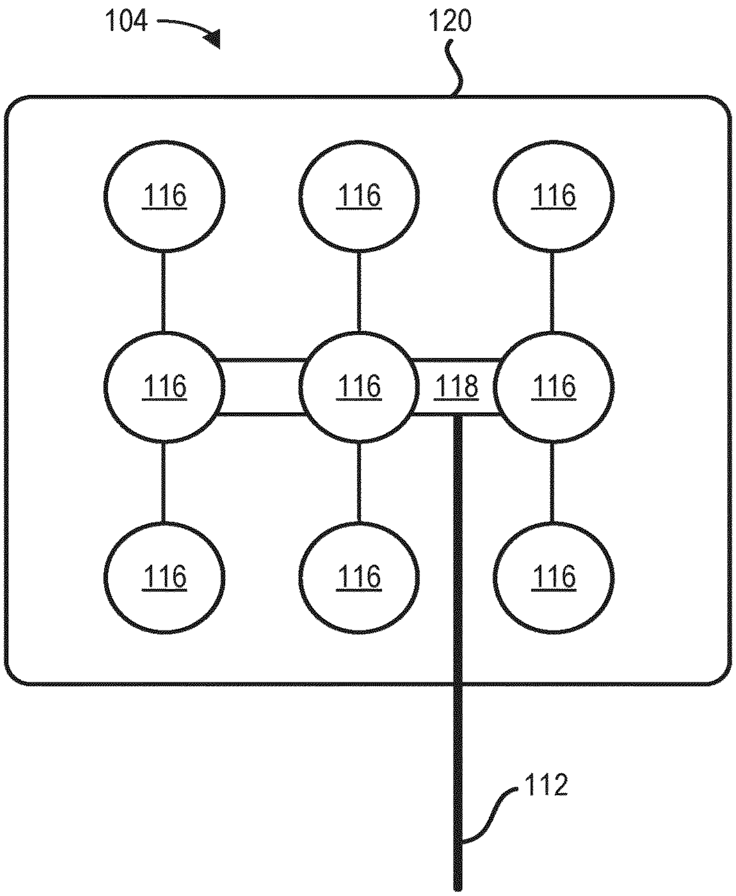
FIG. 2 shows an example transducer array.

The one or more transducer arrays 104 may vary in size and may comprise varying numbers of electrodes 116, based on patient body sizes and/or different therapeutic treatments. For example, in the context of the chest of a patient, small transducer arrays may comprise 13 electrodes each, and large transducer arrays may comprise 20 electrodes each, with the electrodes serially interconnected in each array. For example, as shown in FIG. 2, in the context of the head of a patient, each transducer array may comprise 9 electrodes each, with the electrodes serially interconnected in each array.

Alternative constructions for the one or more transducer arrays 104 are contemplated and may also be used, including, for example, transducer arrays that use ceramic elements that are not disc-shaped, and transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array would be implemented using a region of a conductive material that is configured for placement against a subject/patient's body, with no insulating dielectric layer disposed between the conductive elements and the body. Other alternative constructions for implementing the transducer arrays may also be used. Any transducer array (or similar device/component) configuration, arrangement, type, and/or the like may be used for the methods and systems described herein as long as the transducer array (or similar device/component) configuration, arrangement, type, and/or the like is (a) capable of delivering TTFields to a subject/patient's body and (b) and may be positioned arranged, and/or placed on a portion of a patient/subject's body as described herein.

Status of the apparatus 100 and monitored parameters may be stored in a memory (not shown) and can be transferred to a computing device over a wired or wireless connection. The apparatus 100 may comprise a display (not shown) for displaying visual indicators, such as power on, treatment on, alarms, and low battery.

Figure 3A:
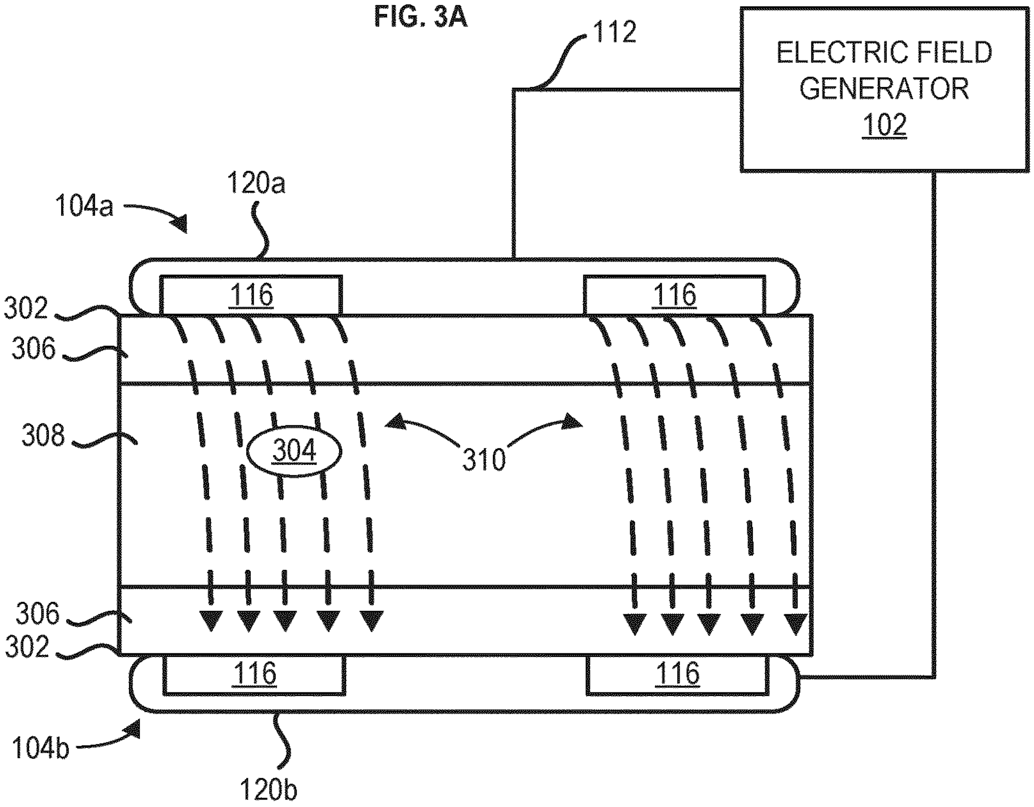
FIG. 3A and FIG. 3B illustrate an example application of the apparatus for electrotherapeutic treatment.
Figure 3B:
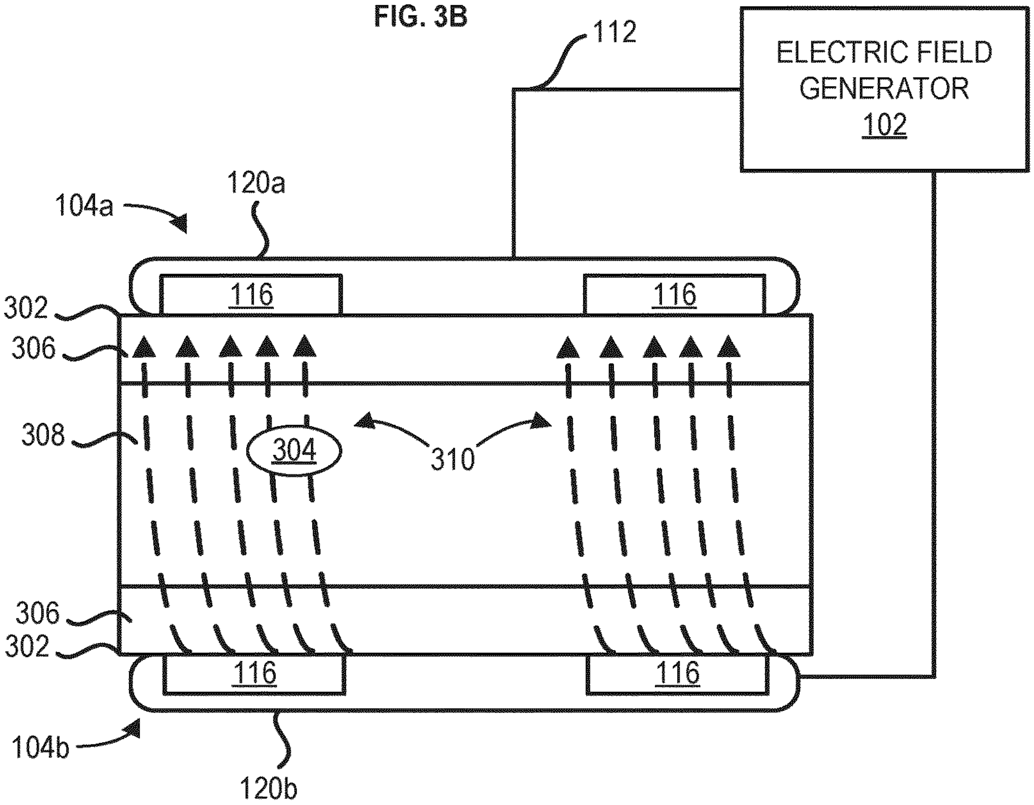

FIG. 3A and FIG. 3B illustrate an example application of the apparatus 100. A transducer array 104*a* and a transducer array 104*b* are shown, each incorporated into a hypoallergenic medical adhesive bandage 120*a* and 120*b*, respectively. The hypoallergenic medical adhesive bandages 120*a* and 120*b* are applied to skin surface 302. A tumor 304 is located below the skin surface 302 and bone tissue 306 and is located within brain tissue 308. The electric field generator 102 causes the transducer array 104*a* and the transducer array 104*b* to generate alternating electric fields 310 within the brain tissue 308 that disrupt rapid cell division exhibited by cancer cells of the tumor 304. The alternating electric fields 310 have been shown in non-clinical experiments to arrest the proliferation of tumor cells and/or to destroy them. Use of the alternating electric fields 310 takes advantage of the special characteristics, geometrical shape, and rate of dividing cancer cells, which make them susceptible to the effects of the alternating electric fields 310. The alternating electric fields 310 alter their polarity at an intermediate frequency (on the order of 100-300 kHz). The frequency used for a particular treatment may be specific to the cell type being treated (e.g., 150 kHz for MPM). The alternating electric fields 310 have been shown to disrupt mitotic spindle microtubule assembly and to lead to dielectrophoretic dislocation of intracellular macromolecules and organelles during cytokinesis. These processes lead to the physical disruption of the cell membrane and programmed cell death (apoptosis).

Because the effect of the alternating electric fields 310 is directional with cells dividing parallel to the field affected more than cells dividing in other directions, and because cells divide in all directions, alternating electric fields 310 may be delivered through two pairs of transducer arrays 104 that generate perpendicular fields within the treated tumor. More specifically, one pair of transducer arrays 104 may be located to the left and right (LR) of the tumor, and the other pair of transducer arrays 104 may be located anterior and posterior (AP) to the tumor. Cycling the alternating electric fields 310 between these two directions (e.g., LR and AP) ensures that a maximal range of cell orientations is targeted. In an embodiment, the alternating electric fields 310 may be delivered according to a symmetric setup of transducer arrays 104 (e.g., four total transducer arrays 104, two matched pairs). In another embodiment, the alternating electric fields 310 may be delivered according to an asymmetric setup of transducer arrays 104 (e.g., three total transducer arrays 104). An asymmetric setup of transducer arrays 104 may engage two of the three transducer arrays 104 to deliver the alternating electric fields 310 and then switch to another two of the three transducer arrays 104 to deliver the alternating electric fields 310, and the like.

In-vivo and in-vitro studies show that the efficacy of TTFields therapy increases as the intensity of the electric field increases. The methods, systems, and apparatuses described are configured for optimizing array placement on the patient's scalp to increase the intensity in the diseased region of the brain.

Figure 4A:
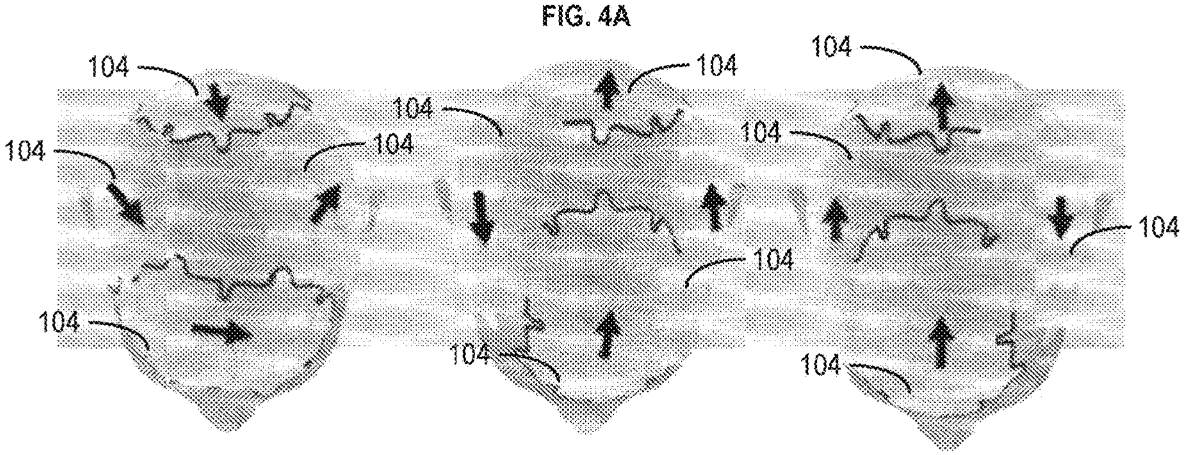
FIG. 4A shows transducer arrays placed on a patient's head.
Figure 4B:
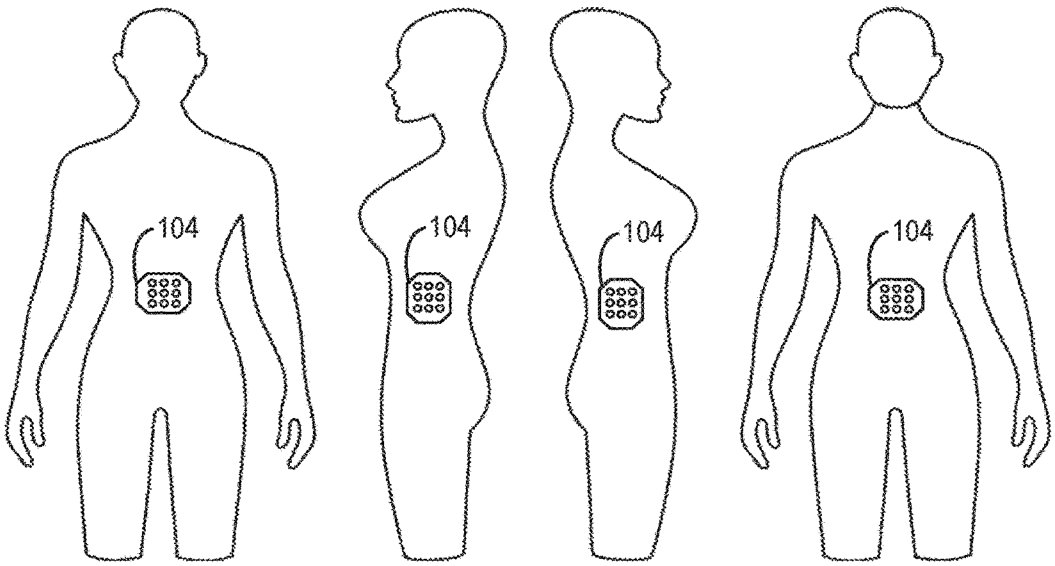
FIG. 4B shows transducer arrays placed on a patient's abdomen.
Figure 5A:
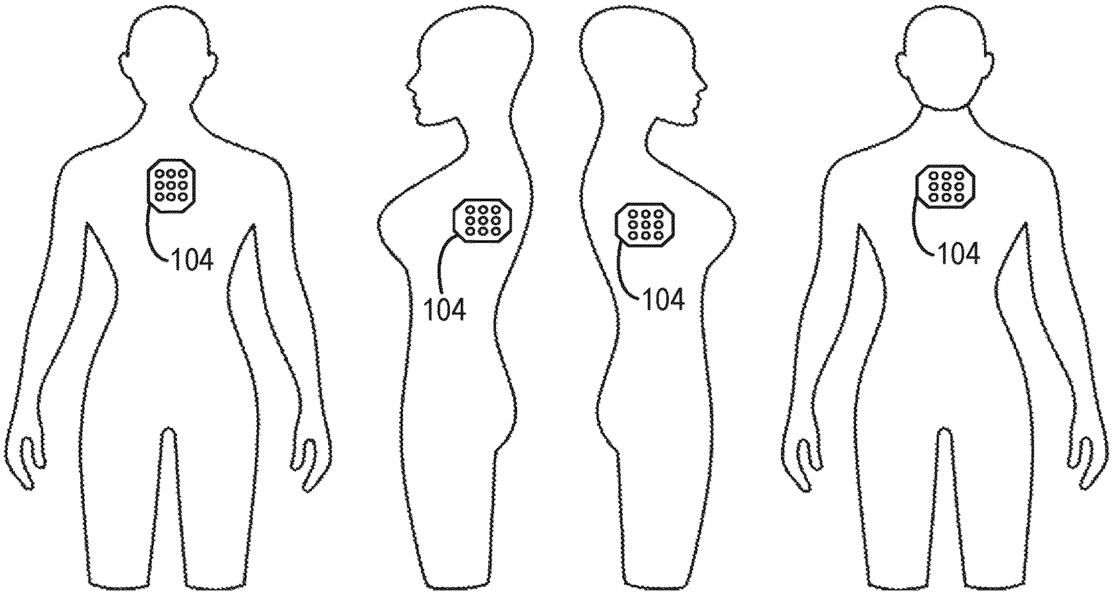
FIG. 5A, the transducer arrays placed on a patient's torso.
Figure 5B:
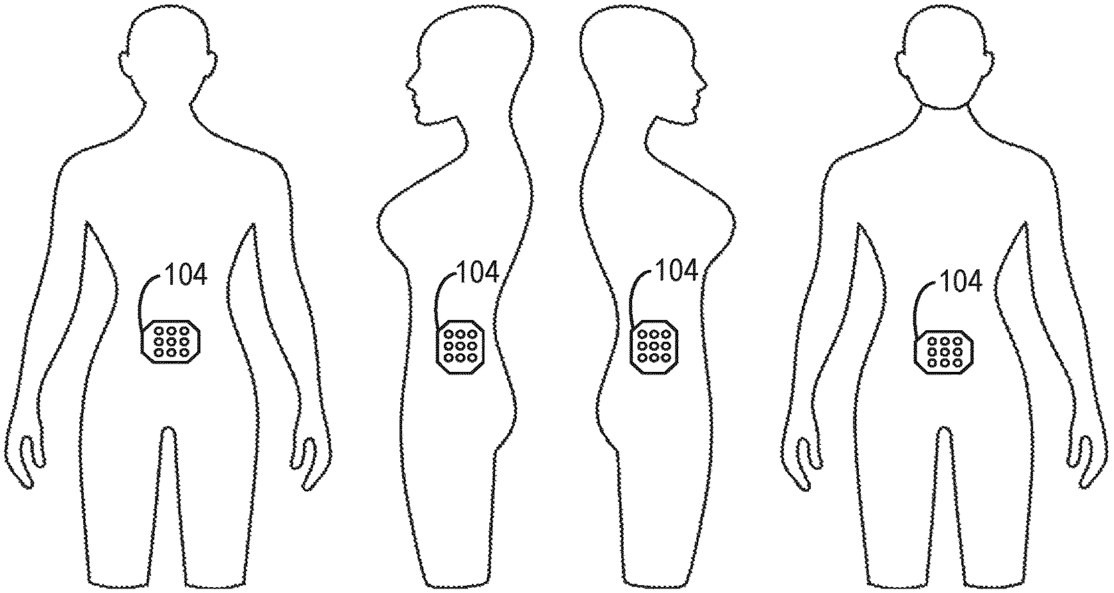
FIG. 5B shows transducer arrays placed on a patient's pelvis

As shown in FIG. 4A, the transducer arrays 104 may be placed on a patient's head. As shown in FIG. 4B, the transducer arrays 104 may be placed on a patient's abdomen. As shown in FIG. 5A, the transducer arrays 104 may be placed on a patient's torso. As shown in FIG. 5B, the transducer arrays 104 may be placed on a patient's pelvis. Placement of the transducer arrays 104 on other portions of a patient's body (e.g., arm, leg, etc.) is specifically contemplated.

Figure 6:
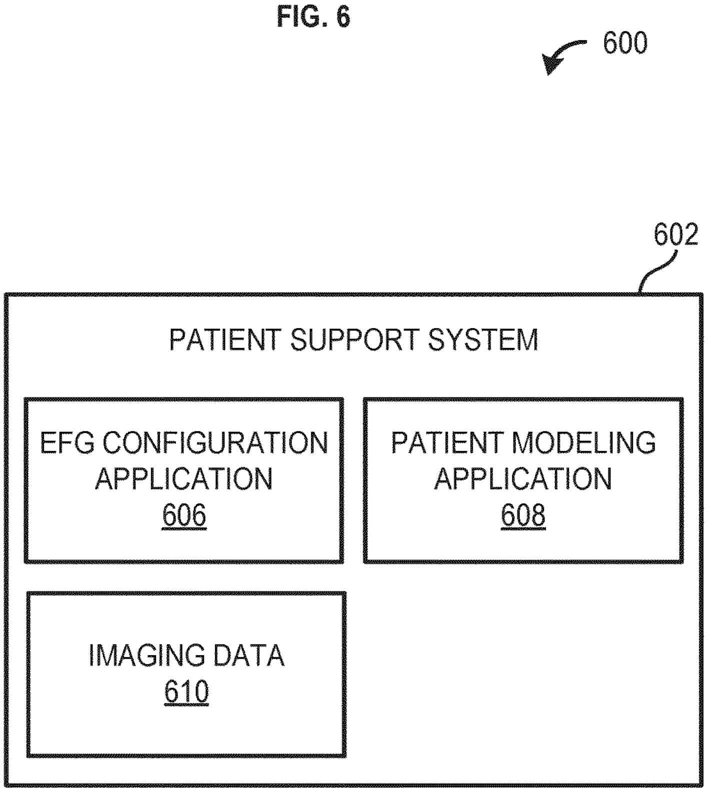
FIG. 6 is a block diagram depicting an electric field generator and a patient support system.

FIG. 6 is a block diagram depicting non-limiting examples of a system 600 comprising a patient support system 602. The patient support system 602 can comprise one or multiple computers configured to operate and/or store an electric field generator (EFG) configuration application 606, a patient modeling application 608, and/or imaging data 610. The patient support system 602 can comprise, for example, a computing device. The patient support system 602 can comprise, for example, a laptop computer, a desktop computer, a mobile phone (e.g., a smartphone), a tablet, and the like.

The patient modeling application 608 may be configured to generate a three dimensional model of a portion of a body of a patient (e.g., a patient model) according to the imaging data 610. The imaging data 610 may comprise any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). The patient modeling application 608 may also be configured to generate a three-dimensional array layout map based on the patient model and one or more electric field simulations.

Figure 7:
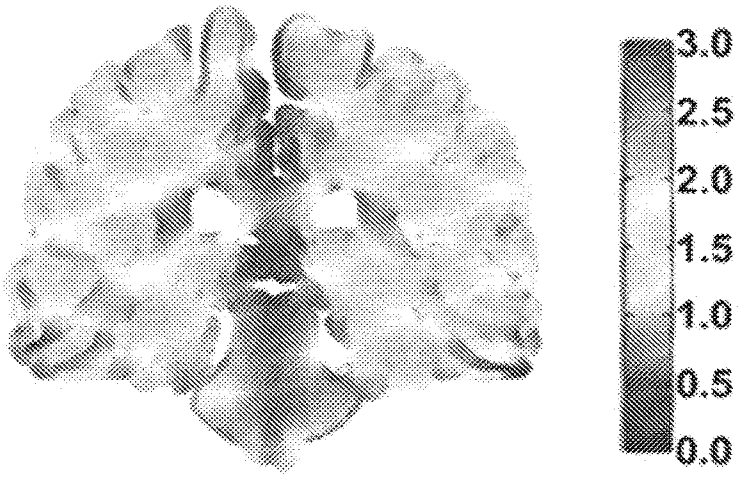
FIG. 7 illustrates electric field magnitude and distribution (in V/cm) shown in coronal view from a finite element method simulation model.

To properly optimize array placement on a portion of a patient's body, the imaging data 610, such as MRI imaging data, may be analyzed by the patient modeling application 608 to identify a region of interest that comprises a tumor. In the context of a patient's head, to characterize how electric fields behave and distribute within the human head, modeling frameworks based on anatomical head models using Finite Element Method (FEM) simulations may be used. These simulations yield realistic head models based on magnetic resonance imaging (MRI) measurements and compartmentalize tissue types such as a skull, white matter, gray matter, and cerebrospinal fluid (CSF) within the head. Each tissue type may be assigned dielectric properties for relative conductivity and permittivity, and simulations may be run whereby different transducer array configurations are applied to the surface of the model to understand how an externally applied electric field, of preset frequency, will distribute throughout any portion of a patient's body, for example, the brain. The results of these simulations, employing paired array configurations, a constant current, and a preset frequency of 200 kHz, have demonstrated that electric field distributions are relatively non-uniform throughout the brain and that electric field intensities exceeding 1 V/cm are generated in most tissue compartments except CSF. These results are obtained assuming total currents with a peak-to-peak value of 1800 milliamperes (mA) at the transducer array-scalp interface. This threshold of electric field intensity is sufficient to arrest cellular proliferation in glioblastoma cell lines. Additionally, by manipulating the configuration of paired transducer arrays, it is possible to achieve an almost tripling of electric field intensity to a particular region of the brain as shown in FIG. 7. FIG. 7 illustrates electric field magnitude and distribution (in V/cm) shown in coronal view from a finite element method simulation model. This simulation employs a left-right paired transducer array configuration.

Figure 8A:
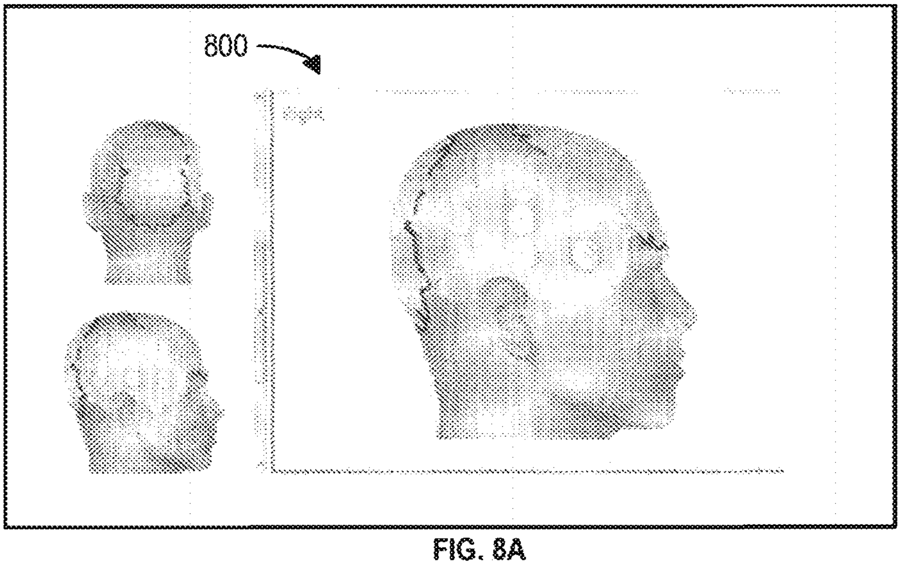
FIG. 8A shows a three-dimensional array layout map 800.
Figure 8B:
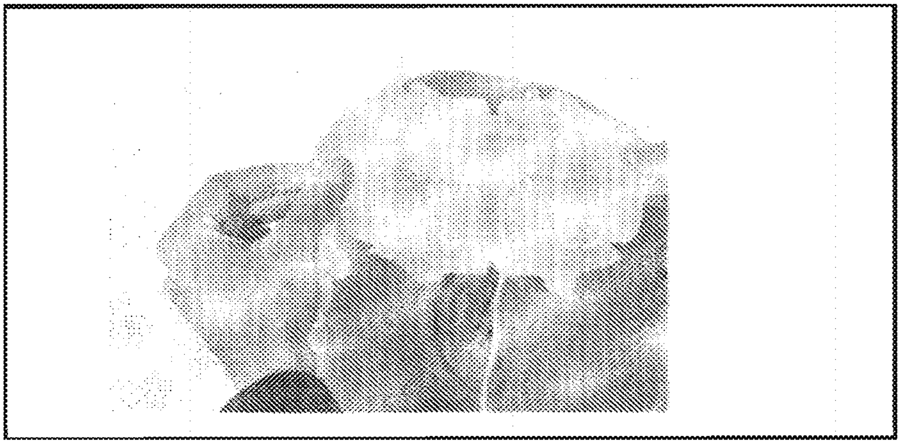
FIG. 8B shows placement of tranducer arrays on the scalp of a patient.

In an aspect, the patient modeling application 608 may be configured to determine a desired (e.g., optimal) transducer array layout for a patient based on the location and extent of the tumor. For example, initial morphometric head size measurements may be determined from the T1 sequences of a brain MRI, using axial and coronal views. Postcontrast axial and coronal MRI slices may be selected to demonstrate the maximal diameter of enhancing lesions. Employing measures of head size and distances from predetermined fiducial markers to tumor margins, varying permutations, and combinations of paired array layouts may be assessed to generate the configuration which delivers maximal electric field intensity to the tumor site. As shown in FIG. 8A, the output may be a three-dimensional array layout map 800. The three-dimensional array layout map 800 may be used by the patient and/or caregiver in arranging arrays on the scalp during the normal course of TTFields therapy as shown in FIG. 8B.

In an aspect, the patient modeling application 608 can be configured to determine the three-dimensional array layout map for a patient. MRI measurements of the portion of the patient that is to receive the transducer arrays may be determined. By way of example, the MRI measurements may be received via a standard Digital Imaging and Communications in Medicine (DICOM) viewer. MRI measurement determination may be performed automatically, for example by way of artificial intelligence techniques, or may be performed manually, for example by way of a physician.

Figure 9A:
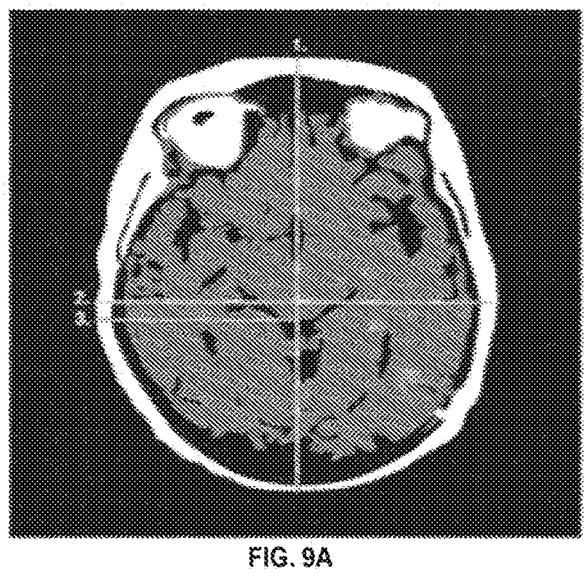
FIG. 9A shows an axial T1 sequence slice containing most apical image, including orbits used to measure head size.
Figure 9B:
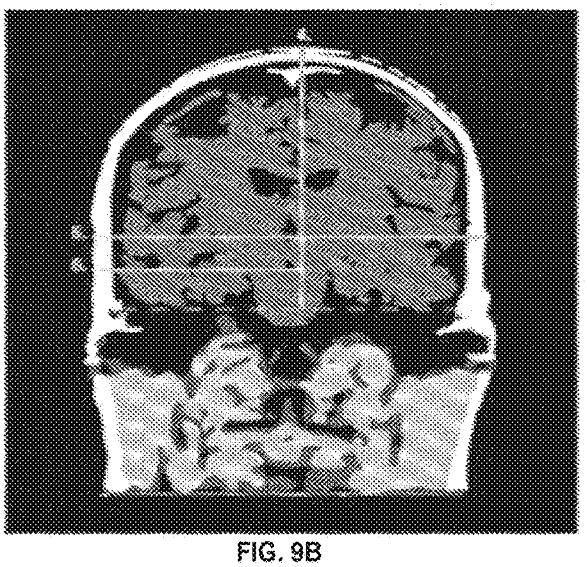
FIG. 9B shows a coronal T1 sequence slice selecting image at level of ear canal used to measure head size.
Figure 9C:
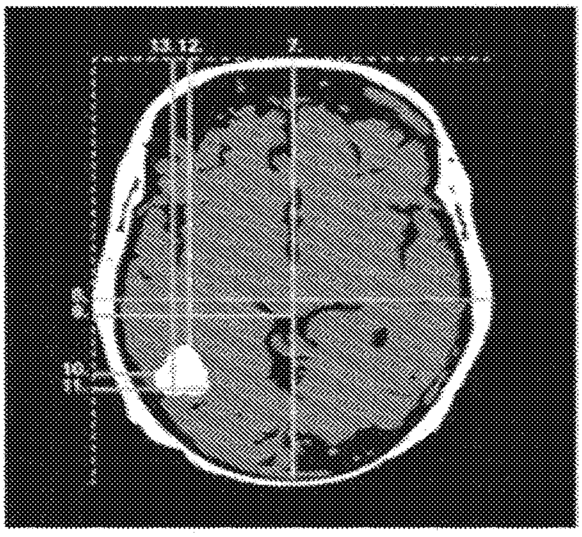
FIG. 9C shows a postcontrast T1 axial image shows maximal enhancing tumor diameter used to measure tumor location.
Figure 9D:
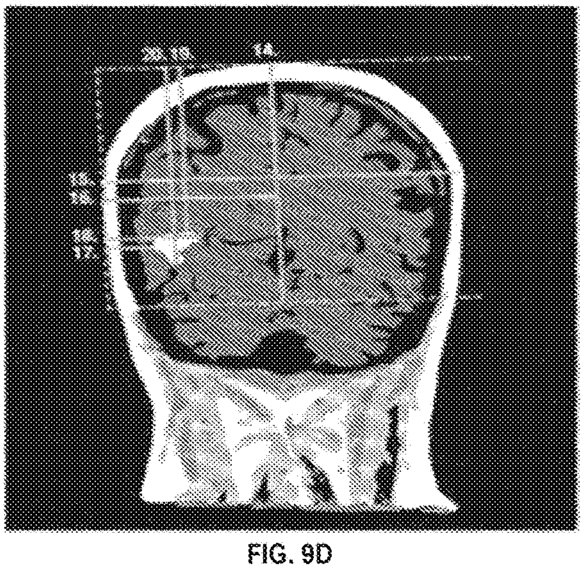
FIG. 9D shows a postcontrast T1 coronal image shows maximal enhancing tumor diameter used to measure tumor location.

Manual MRI measurement determination may comprise receiving and/or providing MRI data via a DICOM viewer. The MRI data may comprise scans of the portion of the patient that contains a tumor. By way of example, in the context of the head of a patient, the MRI data may comprise scans of the head that comprise one or more of a right frontotemporal tumor, a right parieto-temporal tumor, a left frontotemporal tumor, a left parieto-occipital tumor, and/or a multi-focal midline tumor. FIG. 9A, FIG. 9B, FIG. 9C, and FIG. 9D show example MRI data showing scans of the head of a patient. FIG. 9A shows an axial T1 sequence slice containing the most apical image, including orbits used to measure head size. FIG. 9B shows a coronal T1 sequence slice selecting image at the level of car canal used to measure head size. FIG. 9C shows a postcontrast T1 axial image shows maximal enhancing tumor diameter used to measure tumor location. FIG. 9D shows a postcontrast T1 coronal image shows maximal enhancing tumor diameter used to measure tumor location. MRI measurements may commence from fiducial markers at the outer margin of the scalp and extend tangentially from a right-, anterior-, superior origin. Morphometric head size may be estimated from the axial T1 MRI sequence selecting the most apical image which still included the orbits (or the image directly above the superior edge of the orbits)

In an aspect, the MRI measurements may comprise, for example, one or more of, head size measurements and/or tumor measurements. In an aspect, one or more MRI measurements may be rounded to the nearest millimeter and may be provided to a transducer array placement module (e.g., software) for analysis. The MRI measurements may then be used to generate the three-dimensional array layout map (e.g., three-dimensional array layout map 800).

The MRI measurements may comprise one or more head size measurements such as a maximal anteroposterior (A-P) head size, commencing measurement from the outer margin of the scalp; a maximal width of the head perpendicular to the A-P measurement: right to left lateral distance; and/or a distance from the far most right margin of the scalp to the anatomical midline.

The MRI measurements may comprise one or more head size measurements such as coronal view head size measurements. Coronal view head size measurements may be obtained on the T1 MRI sequence selecting the image at the level of the car canal (FIG. 9B). The coronal view head size measurements may comprise one or more of: a vertical measurement from the apex of the scalp to an orthogonal line delineating the inferior margin of the temporal lobes; a maximal right to left lateral head width; and/or a distance from the far right margin of the scalp to the anatomical midline.

The MRI measurements may comprise one or more tumor measurements, such as tumor location measurements. The tumor location measurements may be made using T1 post-contrast MRI sequences, firstly on the axial image demonstrating maximal enhancing tumor diameter (FIG. 9C). The tumor location measurements may comprise one or more of: a maximal A-P head size, excluding the nose; a maximal right to left lateral diameter, measured perpendicular to the A-P distance; a distance from the right margin of the scalp to the anatomical midline; a distance from the right margin of the scalp to the closest tumor margin, measured parallel to the right-left lateral distance and perpendicular to the A-P measurement; a distance from the right margin of the scalp to the farthest tumor margin, measured parallel to the right-left lateral distance, perpendicular to the A-P measurement; a distance from the front of the head, measured parallel to the A-P measurement, to the closest tumor margin; and/or a distance from the front of the head, measured parallel to the A-P measurement, to the farthest tumor margin.

The one or more tumor measurements may comprise coronal view tumor measurements. The coronal view tumor measurements may comprise identifying the postcontrast T1 MRI slice featuring the maximal diameter of tumor enhancement (FIG. 9D). The coronal view tumor measurements may comprise one or more of: a maximal distance from the apex of the scalp to the inferior margin of the cerebrum. In anterior slices, this would be demarcated by a horizontal line drawn at the inferior margin of the frontal or temporal lobes, and posteriorly, it would extend to the lowest level of visible tentorium; a maximal right to left lateral head width; a distance from the right margin of the scalp to the anatomical midline; a distance from the right margin of the scalp to the closest tumor margin, measured parallel to the right-left lateral distance; a distance from the right margin of the scalp to the farthest tumor margin, measured parallel to the right-left lateral distance; a distance from the apex of the head to the closest tumor margin, measured parallel to the superior apex to inferior cerebrum line; and/or a distance from the apex of the head to the farthest tumor margin, measured parallel to the superior apex to inferior cerebrum line.

Other MRI measurements may be used, particularly when the tumor is present in another portion of the patient's body.

The MRI measurements may be used by the patient modeling application 608 to generate a patient model. The patient model may then be used to determine the three-dimensional array layout map (e.g., three-dimensional array layout map 800). Continuing the example of a tumor within the head of a patient, a healthy head model may be generated which serves as a deformable template from which patient models can be created. When creating a patient model, the tumor may be segmented from the patient's MRI data (e.g., the one or more MRI measurements). Segmenting the MRI data identifies the tissue type in each voxel, and electric properties may be assigned to each tissue type based on empirical data. Table 1 shows the standard electrical properties of tissues that may be used in simulations. The region of the tumor in the patient MRI data may be masked, and non-rigid registration algorithms may be used to register the remaining regions of the patient head on to a 3D discrete image representing the deformable template of the healthy head model. This process yields a non-rigid transformation that maps the healthy portion of the patient's head in to the template space, as well as the inverse transformation that maps the template in to the patient space. The inverse transformation is applied to the 3D deformable template to yield an approximation of the patient's head in the absence of a tumor. Finally, the tumor (referred to as a region-of-interest (ROI)) is planted back into the deformed template to yield the full patient model. The patient model may be a digital representation in three-dimensional space of the portion of the patient's body, including internal structures, such as tissues, organs, tumors, etc.

TABLE 1

| Tissue Type | Conductivity, S/m | Relative Permittivity |
|---|---|---|
| Scalp | 0.3 | 5000 |
| Skull | 0.08 | 200 |
| Cerebrospinal fluid | 1.79 | 110 |
| Gray matter | 0.25 | 3000 |
| White matter | 0.12 | 2000 |
| Enhancing tumor | 0.24 | 2000 |
| Enhancing nontumor | 0.36 | 1170 |
| Resection cavity | 1.79 | 110 |
| Necrotic tumor | 1 | 110 |
| Hematoma | 0.3 | 2000 |
| Ischemia | 0.18 | 2500 |
| Atrophy | 1 | 110 |
| Air | 0 | 0 |

Figure 10:
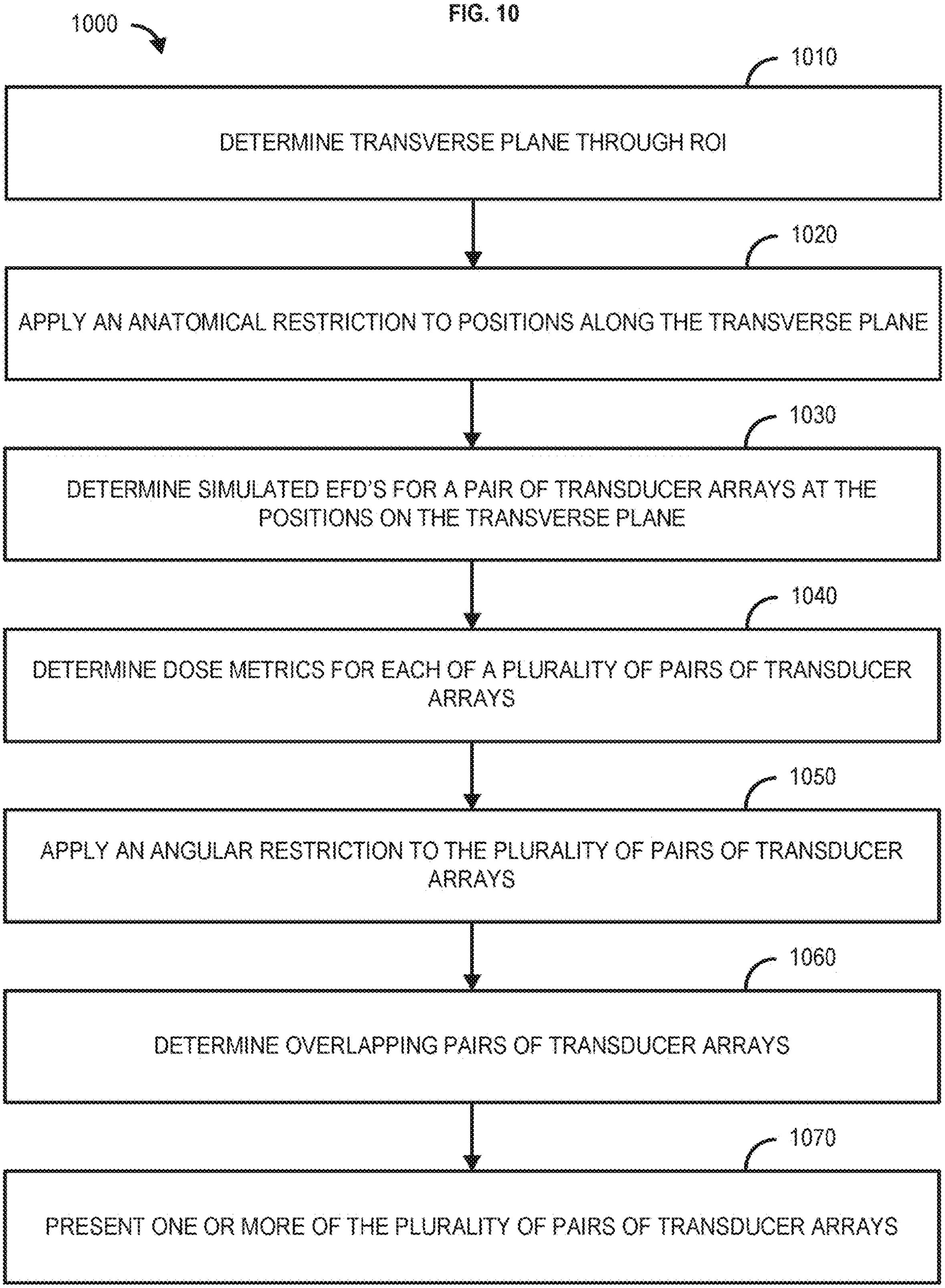
FIG. 10 shows an example optimization method.
Figure 11A:
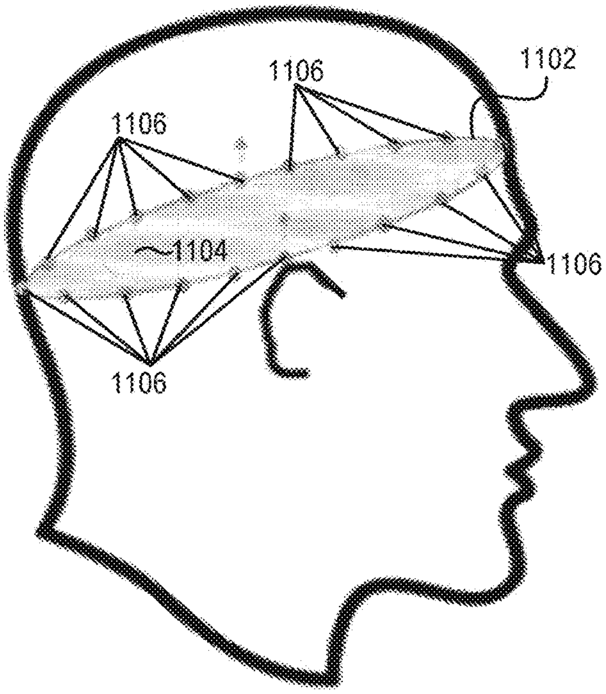
FIG. 11A shows an example transverse plan based on a center point of a tumor in a head of a patient.

Delivery of TTFields may then be simulated by the patient modeling application 608 using the patient model. In an embodiment, the patient modeling application 608 may be configured to perform a method 1000, shown in FIG. 10. The method 1000 can efficiently identify an optimal transducer array layout that delivers high doses (electric fields) to a region-of-interest (ROI) (e.g., a tumor). The method 1000 may comprise determining a transverse plane through an ROI at step 1010. To ensure systematic positioning of the transducer arrays relative to the ROI (e.g., a tumor location), a reference coordinate system may be defined. As shown in FIG. 11A, a transverse plane 1102 may initially be defined by a center of the region of interest 1104 and an inclination angle. The inclination angle may be defined by skill in the art. By way of example, the inclination angle for the head may be 150-20 degrees off the axial plane (e.g., horizontal). The transverse plane 1102 may comprise a contour that is created by a boundary (e.g., outline) of the anatomical model (e.g., the head, the chest, the torso, the abdomen, the leg, the arm, and the like). For example, the contour may resemble an ellipse, a circle, an irregular shape, and the like. Determining the transverse plane 1102 may comprise determining a plurality of positions 1106 along the contour of the transverse plane 1102. The plurality of positions 1106 may represent a location where a transducer array may be affixed to the patient. The plurality of positions 1106 may be determined such that an electric field generated by a transducer array at each position will pass through the ROI 1104. Any number of positions 1106 is contemplated. In an embodiment, the positions 1106 may be divided into pairs, such that an alternating electric field generated by a pair of transducer arrays (each transducer array located at one position of the pair of positions) will pass through the ROI 1104. The positions 1106 may be spaced apart, for example, by 15 degrees, corresponding to approximately 2 cm translations, giving a total of twelve different positions in the range of 180 degrees. Other spacings are contemplated.

Figure 11B:
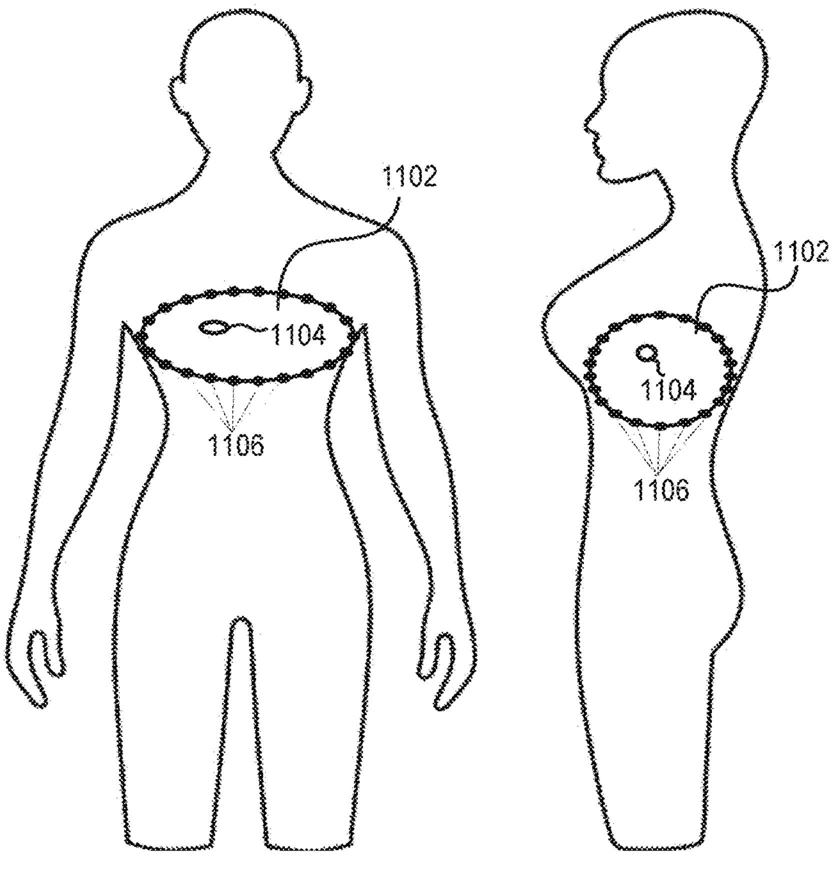
FIG. 11B shows an example transverse plan based on a center point of a tumor in a chest of a patient.

FIG. 11A shows a definition of the transverse plane 1102 in a head of a patient and FIG. 11B shows the transverse plane 1102 as defined in the chest of a patient. The transverse plane 1102 may be defined in any portion of the patient's body.

Returning to FIG. 10, after determining the transverse plane 1102 through the ROI 1104 and the plurality of positions 1106 at step 1010, the method 1000 may apply an anatomical restriction to the positions 1106 at step 1020. The anatomical restriction may be determined based on the patient model and/or by observation. The anatomical restriction may be associated with an anatomical feature of the patient, for example, eyes, cars, joints, armpits, nipples, genitals, and the like. The anatomical restriction may be associated with an area of the patient that should be avoided for transducer array placement because of discomfort or pain that may be caused to the patient, for example, areas of irritation, wounds, scars, and the like.

Figure 12:
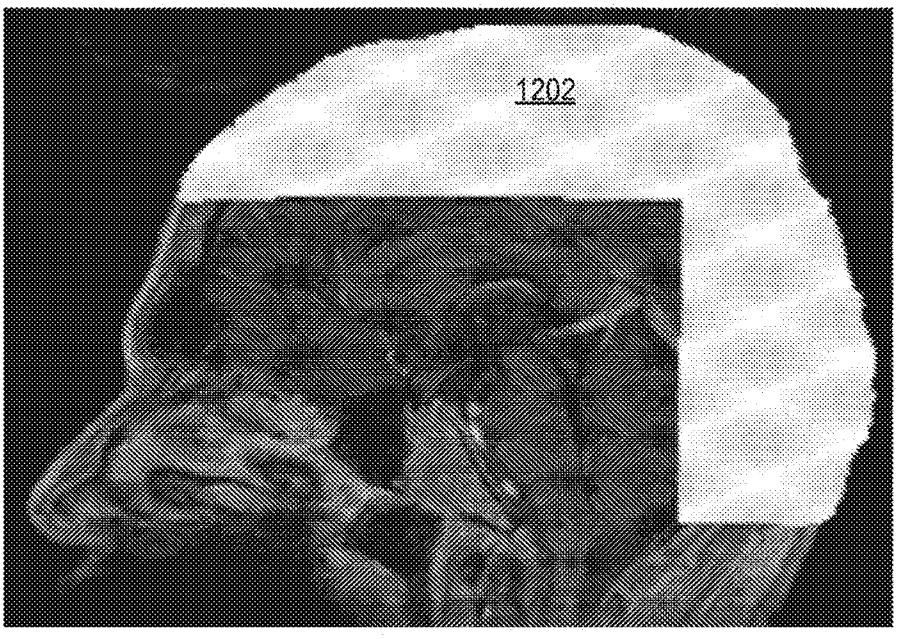
FIG. 12 shows an example atlas.

Application of the anatomical restriction ensures that only anatomically valid locations are considered for transducer array placement. The patient modeling application 608 may be configured to determine the anatomical restriction. In an embodiment, the anatomical restriction may be determined by generating an atlas that comprises the image data a portion of the patient (e.g., MRI data of the head) and a binary image. The binary image may be created manually by an expert segmenting valid portions of the image data. FIG. 12 shows an example atlas created by combining an MRI image of a head and a binary image. An expert manually segmented a valid zone 1202 on the atlas MRI and the valid zone 1202 was saved as a binary image. For example, the valid zones 1202 may be associated with '1's in the binary image. In an embodiment, the same binary image may be used for multiple patients. In another embodiment, a binary image may be generated for each patient.

Figure 13A:
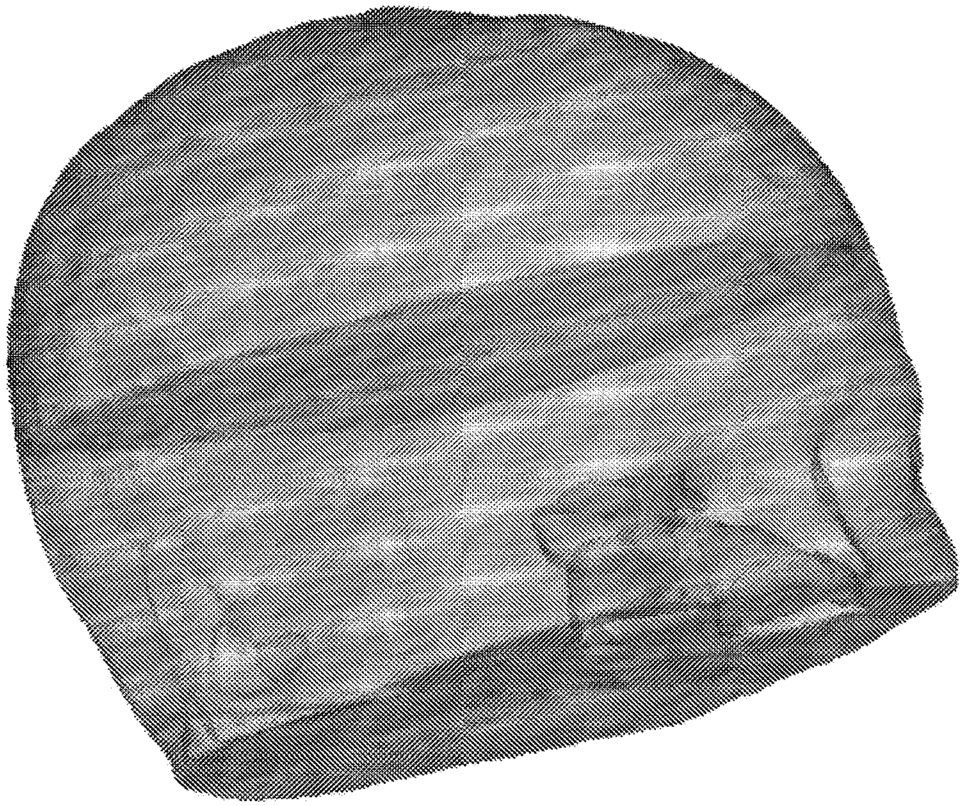
FIGS. 13A-13B show a patient model indicating valid and invalid locations for a transducer array (e.g., anatomical restriction).
Figure 13B:
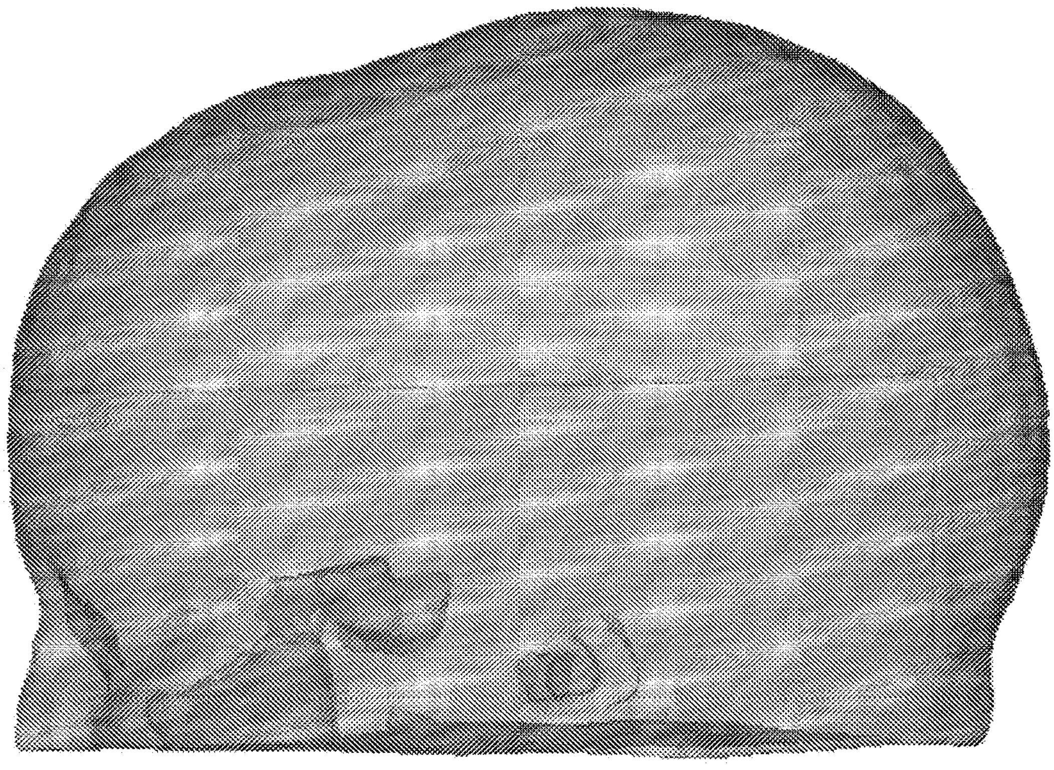

Given a patient model of a new patient, a transform that aligns the atlas to the patient model may be computed and applied to the binary image, masking the valid zones. The binary image may then be modified to fit the patient model boundaries. FIG. 13A and FIG. 13B show a patient model with a valid surface (green) indicated on the patient's head surface (grey). From the patient model, two valid surfaces may be determined one surface for vertical layouts and one surface for horizontal layouts. The surfaces may comprise points and triangles. Each point in the green area may represent an anatomically valid location for transducer array placement, whereas the grey area represents the anatomical restriction.

Figure 14:
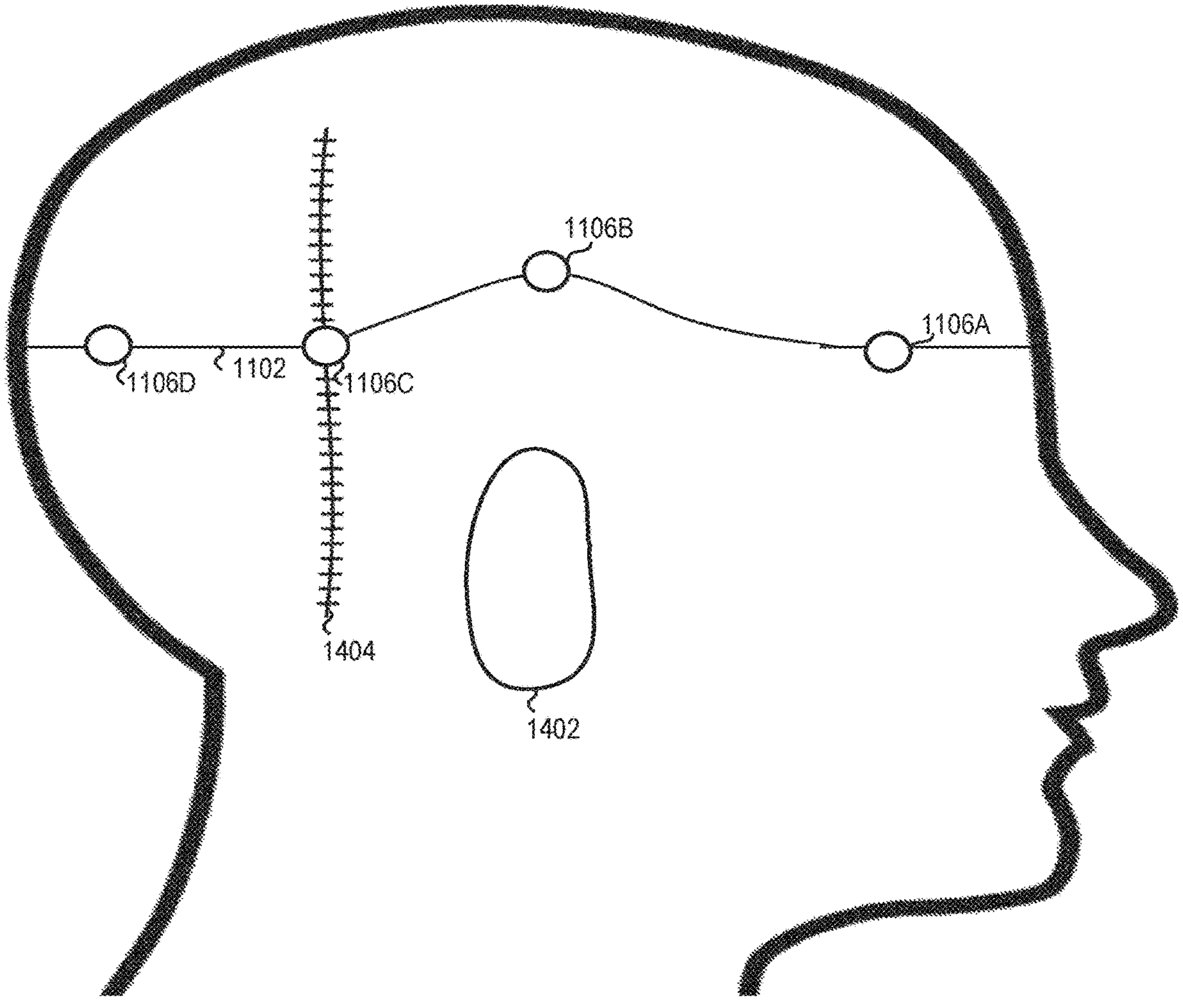
FIG. 14 shows application of an anatomical restriction to positions on a contour of a transverse plane.

In an embodiment, the anatomical restriction may define one or more positions 1106 of the transverse plane 1102 that should be excluded from use in determining electric field distributions. In an embodiment, the anatomical restriction may define one or more positions 1006 of the transverse plane 1002 that should be moved (e.g., raised, lowered, shifted, and the like) to account for the anatomical restriction. As shown in FIG. 14, a position 1106B may be raised to avoid an anatomical restriction 1402 (an car), which adjusts the contour of the transverse plane 1102 to be a 3D curved contour. A position 1106C may be excluded from further analysis as placement of a transducer array at the position 1106C would result in placing the transducer array on an anatomical restriction 1404 (a scar).

Figure 15:
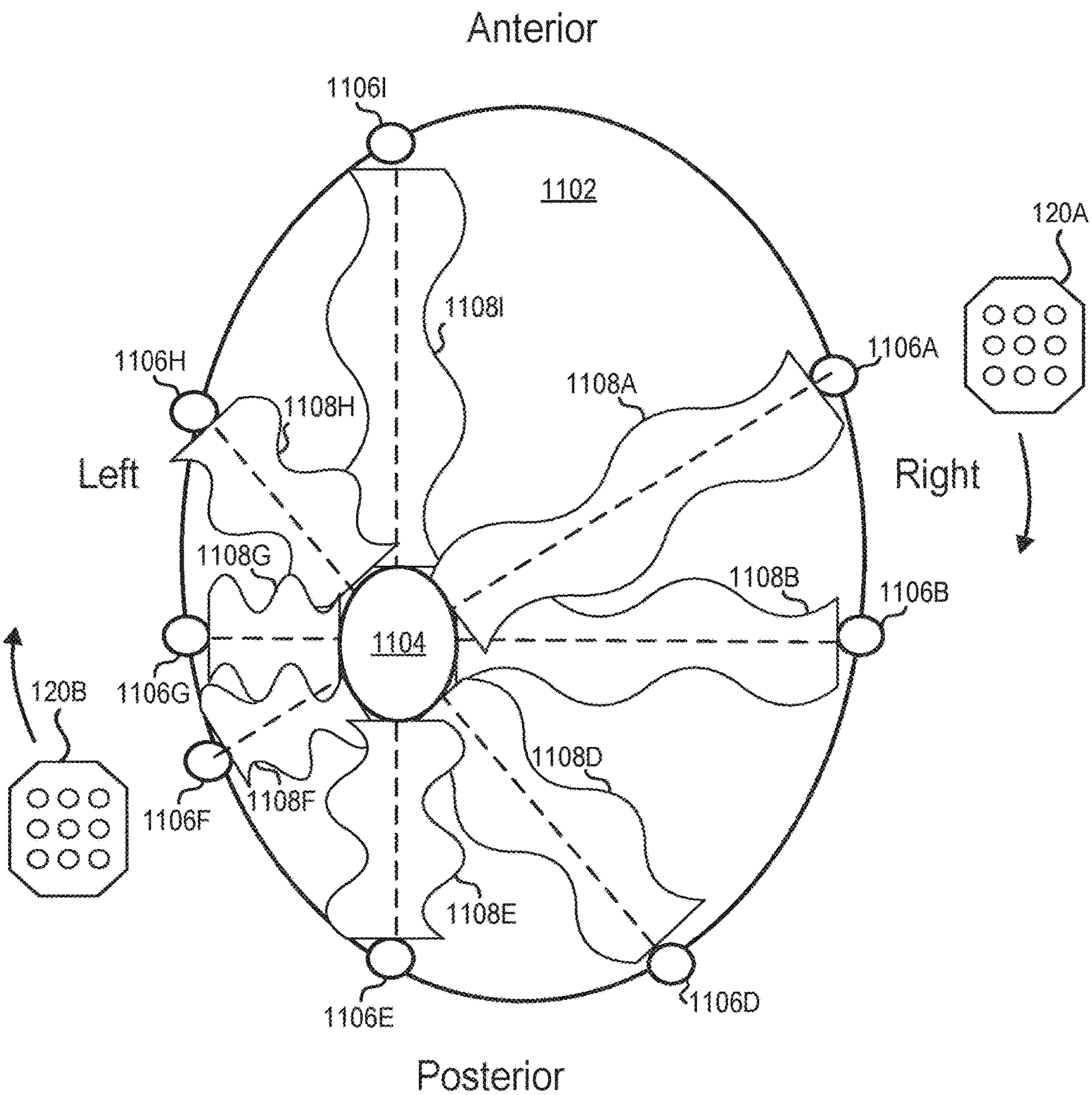
FIG. 15 shows rotation of a pair of transducer array along on a contour of a transverse plane through a head.
Figure 16:
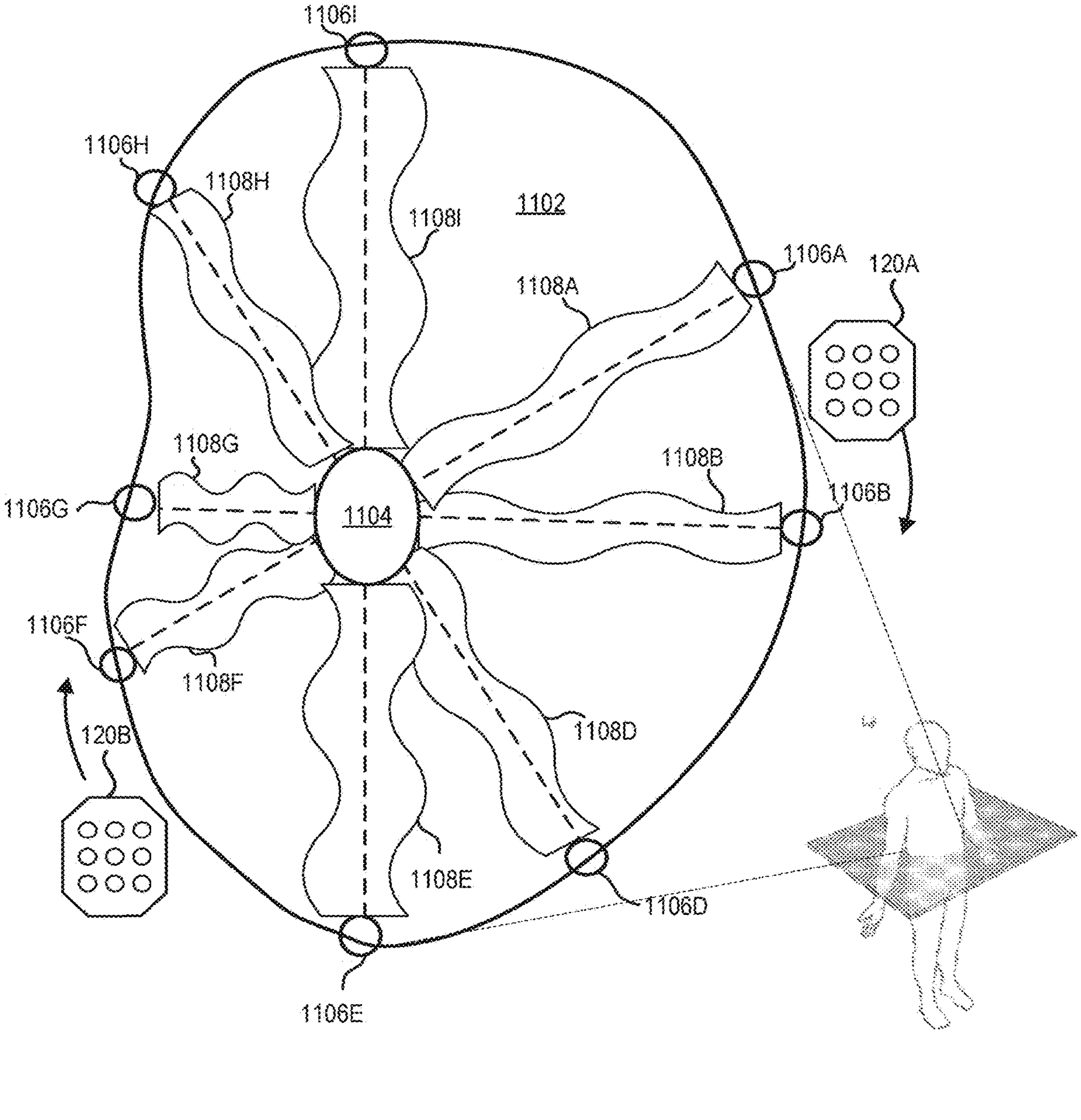
FIG. 16 shows rotation of a pair of transducer array along on a contour of a transverse plane through a chest.

Returning to FIG. 10, after application of the anatomical restriction at step 1020, the method 1000 may determine simulated electric field distributions for a pair of transducer arrays at the positions 1106 of the transverse plane 1102. In an embodiment, as shown in FIG. 15, transducer arrays 120A, 120B (not shown to scale) may be virtually placed with their centers and longitudinal axes along opposing positions 1106 defined along the edge of the transverse plane 1102, wherein the transverse plane 1102 passes through the head of a patient. Opposing positions 1106 include positions that lie along a centerline that intersects with the ROI 1104. As shown in FIG. 15, the opposing positions include, 1106A:1106F, 1106B:1106G, 1106D:1106H, and 1106E:1106I. The centerlines are indicated by dashed lines connecting opposing positions 1106. The centerlines may represent the path of an electric field 1108 generated by either transducer array at either position 1106 of opposing positions 1106. FIG. 16 shows transducer arrays 120A, 120B (not shown to scale) may be virtually placed with their centers and longitudinal axes along opposing positions 1106 defined along the edge of the transverse plane 1102, wherein the transverse plane 1102 passes through a torso of a patient.

Returning to FIG. 15, in an embodiment, the pair of transducer arrays 120A, 120B may be initially placed at any opposing positions 1106 and rotated around the transverse plane 1102 to each pair of opposing positions 1106 from 0-180 degrees, thereby covering the entire circumference of the transverse plane 1002. For example, the pair of transducer arrays 120A, 120B may be virtually placed at opposing positions 1106A:1106F, a simulated electric field distribution may be determined, the pair of transducer arrays 120A, 120B may be rotated around the transverse plane 1102 to opposing positions 1106B:1106G, a simulated electric field distribution may be determined, the pair of transducer arrays 120A, 120B may be rotated around the transverse plane 1102 to opposing positions 1106D:1106H, a simulated electric field distribution may be determined, the pair of transducer arrays 120A, 120B may be rotated around the transverse plane 1102 to opposing positions 1106E:1106I, and a final simulated electric field distribution may be determined. As shown in Table 2, a TTFields distribution map may be generated containing the simulated electric field distributions for each pair of positions.

TABLE 2

| Transducer Array 120A | Transducer Array 120B | EFD |
|---|---|---|
| 1106A | 1106F | EFD Simulation 1 |
| 1106B | 1106G | EFD Simulation 2 |
| 1106D | 1106H | EFD Simulation 3 |
| 1106E | 1106I | EFD Simulation 4 |

Returning to FIG. 10, after the simulated electric field distributions are determined at step 1030, the method 1000 may proceed to step 1040 to determine dose metrics for each of a plurality of pairs of transducer arrays. In an embodiment, the method 1000 may determine a dose metric based on an electric field distribution determined for each of two pairs of transducer arrays 120. Simulated electric field distributions, dosimetry, and simulation-based analysis are described in U.S. Patent Publication No. 20190117956 A1 and Publication "Correlation of Tumor Treating Fields Dosimetry to Survival Outcomes in Newly Diagnosed Glioblastoma: A Large-Scale Numerical Simulation-based Analysis of Data from the Phase 3 EF-14 randomized Trial" by Ballo, et al. (2019) which are incorporated herein by reference in their entirety. The dose metric in the ROI may be determined for all possible position 1106 combinations of two pairs of transducer arrays 120. Table 3 indicates the results of determining the dose metrics at step 1040.

TABLE 3

| Transducer Array Pair 1 | Transducer Array Pair 2 | Dose Metric |
|---|---|---|
| 1106A: 1106F | 1106B: 1106G | Dose Metric 1 |
| 1106A: 1106F | 1106D: 1106H | Dose Metric 2 |
| 1106A: 1106F | 1106E: 1106I | Dose Metric 3 |
| 1106B: 1106G | 1106D: 1106H | Dose Metric 4 |
| 1106B: 1106G | 1106E: 1106I | Dose Metric 5 |
| 1106D: 1106H | 1106E: 1106I | Dose Metric 6 |

After the dose metrics are determined at step 1040, the method 1000 may proceed to step 1050 to apply an angular restriction to the plurality of pairs of transducer arrays. In an embodiment, the method 1000 may determine one or more candidate transducer array layout plans according to the angular restriction at step 1050. The angular restriction may indicate a restriction with regard to transducer array position relative to other transducer arrays. The angular restriction may be determined based on a number of desired pairs of transducer arrays. In an embodiment, the angular restriction may be determined by dividing 180 degrees by the number of desired transducer array pairs. For example, if two pairs of transducer arrays are desired, the angular restriction may be approximately 90 degrees. In an embodiment where three pairs of transducer arrays are desired, the angular restriction may be approximately 60 degrees. In an embodiment where four pairs of transducer arrays are desired, the angular restriction may be approximately 45 degrees. The angular restriction may specify that a transducer array pair should be positioned such that the angular restriction is satisfied for at least one other transducer array pair. The angular restriction may be assessed based on the centerlines between the positions 1106 where the pairs of transducer arrays are located.

The angular restriction may eliminate from consideration transducer array positions that cause transducer array positions to fall within or fall outside of the angular restriction. For example, the angular restriction may indicate that only transducer array positions that create an orthogonal (90 degree) angle between two pairs of transducer arrays be considered. Any angle may be contemplated with the angular restriction. The angular restriction may further comprise a range. The range may be for example, between 30-90 degrees. In an embodiment, the size of the transducer arrays may impact the angular restriction. The smaller the transducer array, the more transducer arrays may be used. Accordingly, the angular restriction may be relatively small (e.g., 30-45 degrees) to account for the increased number of smaller transducer arrays.

Figure 17:
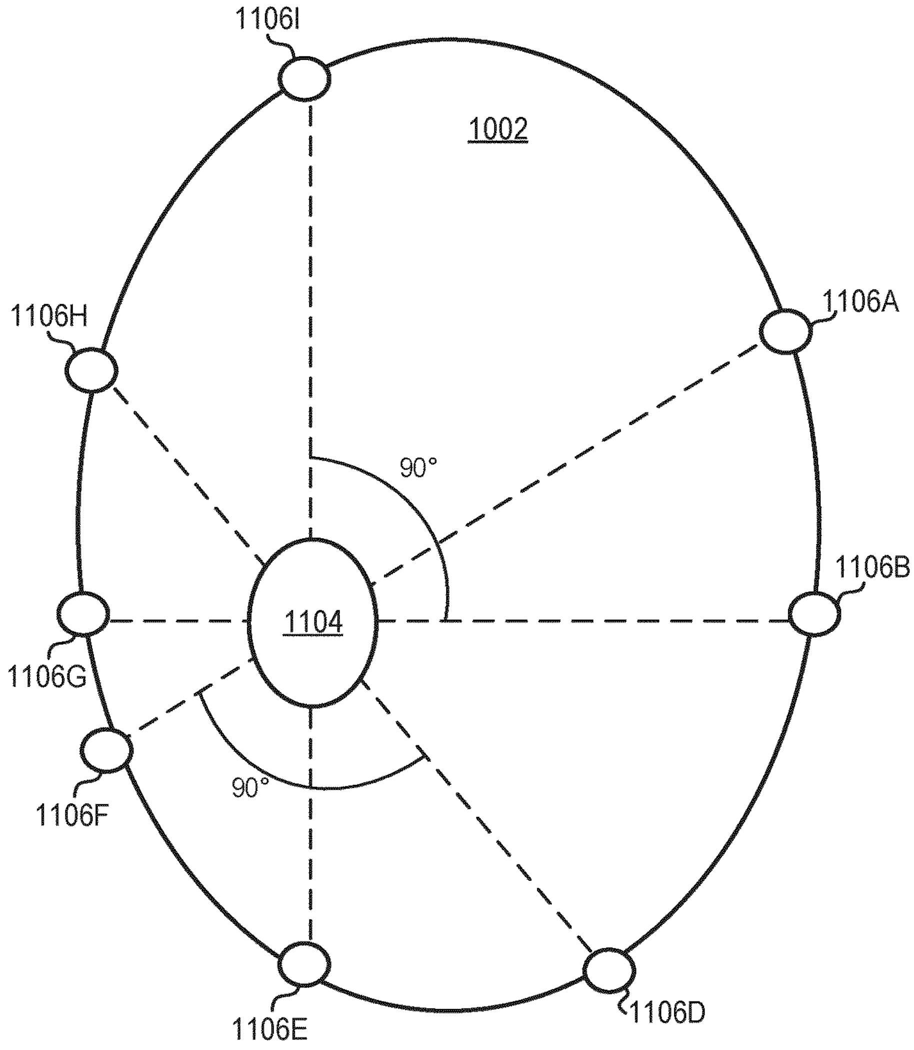
FIG. 17 shows the application of an angular restriction to positions on a contour of a transverse plane.

At step 1050, the method 1000 may determine an angle between each combination of two pairs of transducer arrays 120. As shown in FIG. 17, the transducer array pair located at position 1106A:1106F is associated with a centerline (dashed line) that is at a 90-degree angle to a centerline associated with another transducer array pair located at position 1106D:1106H. The transducer array pair located at position 1106A:1106F is associated with a centerline (dashed line) that is at a 30-degree angle to a centerline associated with another transducer array pair located at position 1106B:1106G. Table 3 shows the results of the determination of dose metrics and angles for the combinations of positions of pairs of transducer arrays 120 shown in FIG. 17.

TABLE 3

| Transducer Array Pair 1 | Transducer Array Pair 2 | Dose Metric | Angle |
|---|---|---|---|
| 1106A: 1106F | 1106B: 1106G | Dose Metric 1 | 30 |
| 1106A: 1106F | 1106D: 1106H | Dose Metric 2 | 90 |
| 1106A: 1106F | 1106E: 1106I | Dose Metric 3 | 120 |
| 1106B: 1106G | 1106D: 1106H | Dose Metric 4 | 60 |
| 1106B: 1106G | 1106E: 1106I | Dose Metric 5 | 90 |
| 1106D: 1106H | 1106E: 1106I | Dose Metric 6 | 30 |

Returning to FIG. 10, at step 1050, one or more candidate transducer array layout plans may be determined by filtering out transducer array pair positions that deviate from the angular restriction. For example, in Table 3, a candidate transducer array layout plan may comprise positions: (1106A:1106F) and (1106D:1106H). Another candidate transducer array layout plan may comprise position 1006 positions: (1106B:1106G) and (1106E:1106I). In an embodiment, candidate transducer array layout plans may be selected that fall outside the angular restriction to allow a user to examine the effect of different transducer array layout plans on the dose density maps and dose metric.

After the angular restriction is applied at step 1050, method 1000 may proceed to step 1060 to determine overlap between transducer arrays. Since the electric field distributions performed in step 1030 were calculated as individual transducer array pairs, the position and orientation of the transducer arrays 120 in each candidate transducer array layout plan may create physical overlaps between neighboring transducer arrays 120. An overlap between neighboring transducer arrays 120 may be created as a result of any portion of a transducer array 120 overlapping with any portion of another transducer array 120. For example, the transducer array 120 may comprise an adhesive bandage designed to keep a transducer array 120 affixed to the patient during treatment. At step 1050, the method 1000 may determine that a likelihood exists that an adhesive bandage of one transducer array 120 may overlap with a portion of another transducer array 120 (for example, overlap with another adhesive bandage, a conductive lead 112, and/or an electrode 116). In another example, at step 1050, the method 1000 may determine that one or more electrodes 116 of a transducer array 120 overlaps with a portion of another transducer array 120 (for example, overlap with another adhesive bandage, a conductive lead 112, and/or an electrode 116). In an embodiment, some overlaps may be ignored, such as overlapping adhesive bandages. In an embodiment, some overlaps may not be ignored, such as overlapping electrodes 116. The patient modeling application 608 may be configured to determine, based on predetermined size information associated with each transducer array whether an overlap exists between transducer arrays and further whether such overlap warrants adjustment of a transducer array (e.g., overlapping electrode vs. overlapping adhesive bandage).

In an embodiment, at step 1060, the method 1000 may, for each candidate transducer array layout plan, cause the transducer arrays 120 to change orientation and/or position to eliminate (or reduce) overlap between transducer arrays 120 In an embodiment, at step 1070, the method 1000 may present one or more of the plurality of pairs of transducer arrays. The patient modeling application 608 may be configured to present one or more candidate transducer array layout plans and/or one or more adjusted candidate transducer array layout plans. In an embodiment, the patient modeling application 608 may present one or more candidate transducer array layout plans and/or one or more adjusted candidate transducer array layout plans for selection as a final transducer array layout plan and/or for further adjustment by a user. The final transducer array layout plan may be determined from the candidate transducer array layout plans and/or the adjusted candidate transducer array layout plans based on the electric field distributions and/or the dose metrics.

Figure 18:
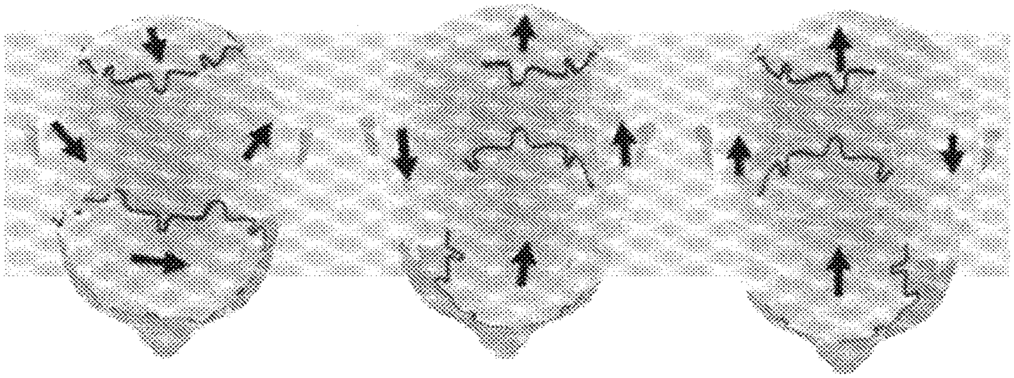
FIG. 18 shows an example interface.

In an embodiment, shown in FIG. 18, one or more candidate transducer array layout plans may be displayed to a user. The user may manipulate the placement of each transducer array and the resulting change in electric field distribution and dose metric may be displayed.

Electric field distributions described above with regard to the optimization method may be determined by the patient modeling application 608 using a finite element (FE) approximation of electrical potential. In general, the quantities defining a time-varying electromagnetic field are given by the complex Maxwell equations. However, in biological tissues and at the low to an intermediate frequency of TTFields (f=200 kHz), the electromagnetic wavelength is much larger than the size of the head and the electric permittivity $\varepsilon$ is negligible compared to the real-valued electric conductivity $\sigma$, i.e., where $\omega=2\pi f$ is the angular frequency. This implies that the electromagnetic propagation effects and capacitive effects in the tissue are negligible, so the scalar electric potential may be well approximated by the static Laplace equation $\nabla\cdot(\sigma\nabla\phi)=0$, with appropriate boundary conditions at the electrodes and skin. Thus, the complex impedance is treated as resistive (i.e. reactance is negligible) and currents flowing within the volume conductor are, therefore, mainly free (Ohmic) currents. The FE approximation of Laplace's equation was calculated using the SimNIBS software (simnibs.org). Computations were based on the Galerkin method and the residuals for the conjugate gradient solver were required to be <1E-9. Dirichlet boundary conditions were used with the electric potential was set to (arbitrarily chosen) fixed values at each set of electrode arrays. The electric (vector) field was calculated as the numerical gradient of the electric potential and the current density (vector field) was computed from the electric field using Ohm's law. The potential difference of the electric field values and the current densities were linearly rescaled to ensure a total peak-to-peak amplitude for each array pair of 1.8 A, calculated as the (numerical) surface integral of the normal current density components over all triangular surface elements on the active electrode discs. This corresponds to the current level used for clinical TTFields therapy by the Optune® device. The "dose" of TTFields was calculated as the intensity (L2 norm) of the field vectors. The modeled current is assumed to be provided by two separate and sequentially active sources each connected to a pair of 3×3 transducer arrays. The left and posterior arrays may be defined to be sources in the simulations, while the right and anterior arrays were the corresponding sinks, respectively. However, as TTFields employ alternating fields, this choice is arbitrary and does not influence the results.

An average electric field strength generated by transducer arrays placed at multiple locations on the patient may be determined by the patient modeling application 608 for one or more tissue types. In an aspect, the transducer array position that corresponds to the highest average electric field strength in the tumor tissue type(s) may be selected as a desired (e.g., optimal) transducer array position for the patient. Accordingly, the transducer array positions that correspond to the highest average electric field strength in the tumor tissue type(s) may be selected as a desired (e.g., optimal) transducer array layout map for the patient. In an embodiment, the method 1000 may be used to determine the transducer array layout map.

The patient model may be modified to include an indication of the desired transducer array layout map. The resulting patient model, comprising the indication(s) of the transducer array layout map, may be referred to as the three-dimensional array layout map (e.g., three-dimensional array layout map 600). The three-dimensional array layout map may thus comprise a digital representation, in three-dimensional space, of the portion of the patient's body, an indication of tumor location, an indication of a position for placement of one or more transducer arrays, combinations thereof, and the like.

The three-dimensional array layout map may be provided to the patient in a digital form and/or a physical form. The patient, and/or a patient caregiver, may use the three-dimensional array layout map to affix one or more transducer arrays to an associated portion of the patient's body (e.g., head).

The three-dimensional array layout map may further comprise an indication of one or more landmarks on the portion of the patient's body (e.g., curves, bumps, crevices, structures (e.g., car, nose, nipple, etc.). The indication of one or more landmarks on the portion of the patient's body may be derived by the patient modeling application 608 from the imaging data. The three-dimensional array layout map may comprise position data indicative of the placement of the one or more transducer arrays on the portion of the body and surface data indicative of one or more landmarks of the portion of the body. Digital three dimensional representation can be used as described in Bücking™, et al. (2017), From medical imaging data to 3D printed anatomical models. PLoS ONE 12(5): e0178540; Ahmed Hosny et al. J Thorac Cardiovasc Surg 2018, 155:143-5, incorporated by reference herein.

Figure 19:
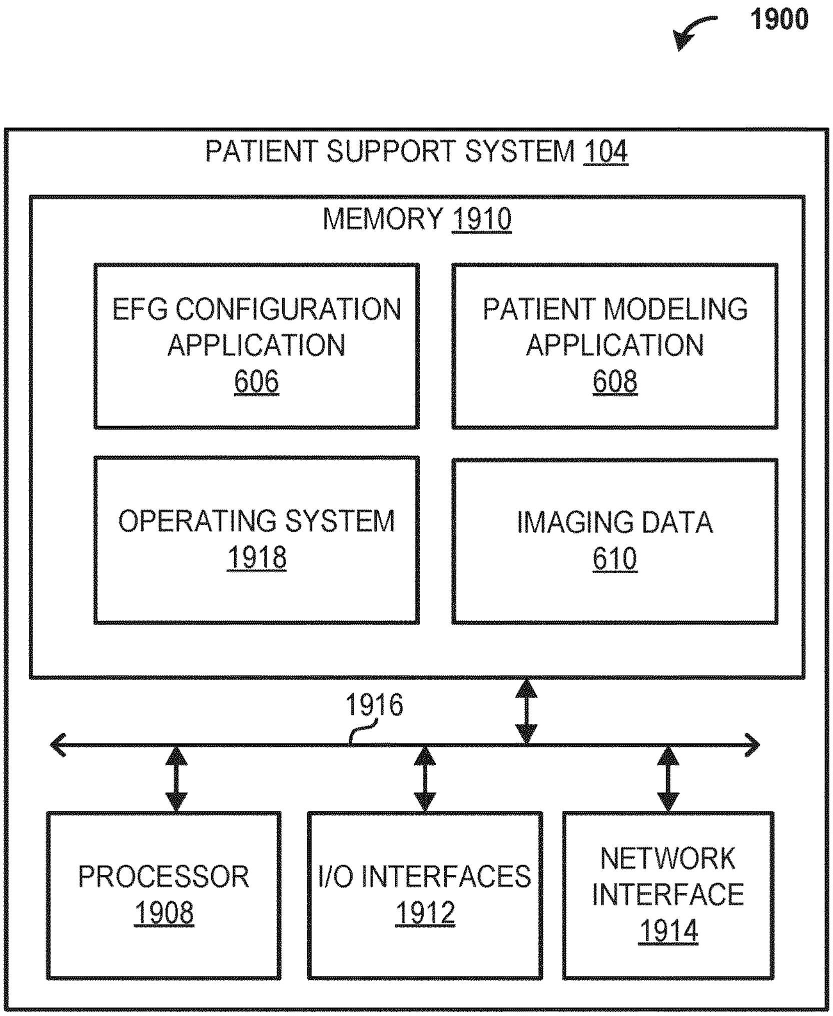
FIG. 19 is a block diagram depicting an example operating environment.

FIG. 19 is a block diagram depicting an environment 1900 comprising a non-limiting example of the patient support system 104. In an aspect, some or all steps of any described method may be performed on a computing device as described herein. The patient support system 104 can comprise one or multiple computers configured to store one or more of the EFG configuration application 606, the patient modeling application 608, the imaging data 610, and the like.

The patient support system 104 can be a digital computer that, in terms of hardware architecture, generally includes a processor 1908, memory system 1910, input/output (I/O) interfaces 1912, and network interfaces 1914. These components (1908, 1910, 1912, and 1914) are communicatively coupled via a local interface 1916. The local interface 1916 can be, for example, but not limited to, one or more buses or other wired or wireless connections, as is known in the art. The local interface 1916 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1908 can be a hardware device for executing software, particularly that stored in the memory system 1910. The processor 1908 can be any custom made or commercially available processor, a central processing unit (CPU), an auxiliary processor among several processors associated with the patient support system 104, a semiconductor-based microprocessor (in the form of a microchip or chipset), or generally any device for executing software instructions. When the patient support system 104 is in operation, the processor 1908 can be configured to execute software stored within the memory system 1910, to communicate data to and from the memory system 1910, and to generally control operations of the patient support system 104 pursuant to the software.

The I/O interfaces 1912 can be used to receive user input from and/or for providing system output to one or more devices or components. User input can be provided via, for example, a keyboard and/or a mouse. System output can be provided via a display device and a printer (not shown). I/O interfaces 1912 can include, for example, a serial port, a parallel port, a Small Computer System Interface (SCSI), an IR interface, an RF interface, and/or a universal serial bus (USB) interface.

The network interface 1914 can be used to transmit and receive from the patient support system 104. The network interface 1914 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1914 may include address, control, and/or data connections to enable appropriate communications.

The memory system 1910 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1910 may incorporate electronic, magnetic, optical, and/or other types of storage media. Note that the memory system 1910 can have a distributed architecture, where various components are situated remote from one another but can be accessed by the processor 1908.

The software in memory system 1910 may include one or more software programs, each of which comprises an ordered listing of executable instructions for implementing logical functions. In the example of FIG. 19, the software in the memory system 1910 of the patient support system 104 can comprise the EFG configuration application 606, the patient modeling application 608, the imaging data 610, and a suitable operating system (O/S) 1918. The operating system 1918 essentially controls the execution of other computer programs, and provides scheduling, input-output control, file and data management, memory management, and communication control and related services.

For purposes of illustration, application programs and other executable program components such as the operating system 1918 are illustrated herein as discrete blocks, although it is recognized that such programs and components can reside at various times in different storage components of the patient support system 104. An implementation of the EFG configuration application 606, the patient modeling application 608, the imaging data 610, and/or the control software 110 can be stored on or transmitted across some form of computer-readable media. Any of the disclosed methods can be performed by computer-readable instructions embodied on computer-readable media. Computer-readable media can be any available media that can be accessed by a computer. By way of example and not meant to be limiting, computer-readable media can comprise "computer storage media" and "communications media." "Computer storage media" can comprise volatile and non-volatile, removable and non-removable media implemented in any methods or technology for storage of information such as computer-readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

Figure 20:
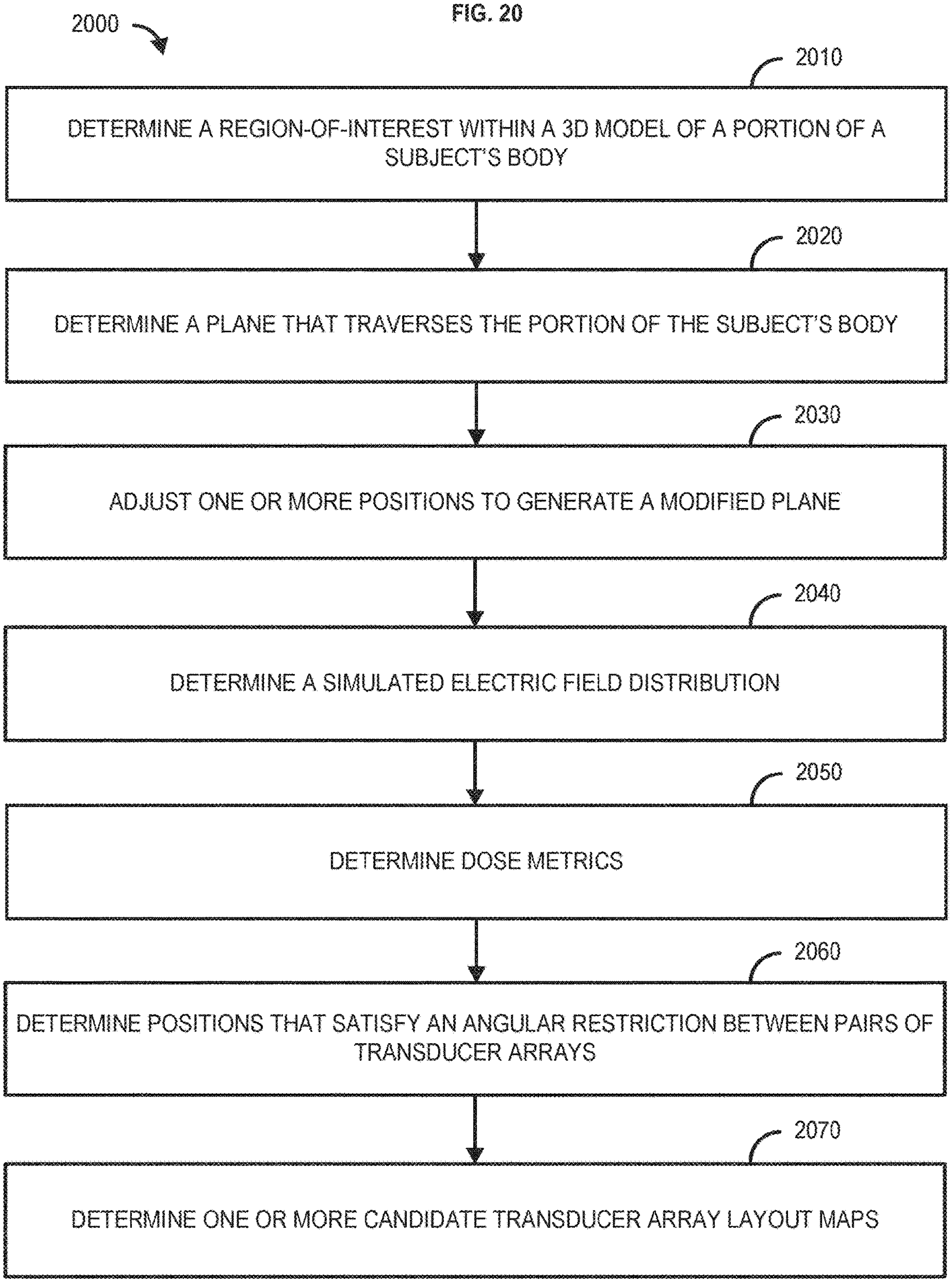
FIG. 20 shows an example method.

In an embodiment, illustrated in FIG. 20, one or more of the apparatus 100, the patient support system 602, the patient modeling application 608, and/any other device/component described herein can be configured to perform a method 2000 comprising, at 2010, determining a region-of-interest (ROI) within a 3D model of a portion of a subject's body.

At 2020, determining, based on a center of the ROI, a plane that transverses the portion of the subject's body, wherein the plane comprises a plurality of pairs of positions along a contour of the plane.

At 2030, adjusting, based on an anatomical restriction, one or more positions of the plurality of pairs of positions to generate a modified plane. The anatomical restriction may be based on an anatomical feature of the portion of the subject's body. For example, a first electric field generated by a first transducer array may be simulated at a first position, a second electric field generated by a second transducer array may be simulated at a second position opposite the first position, and, based on the first electric field and the second electric field, the simulated electric field distribution may be determined. In some instances, a third electric field generated by the first transducer array may be simulated at a third position, and a fourth electric field generated by the second transducer array may be simulated at a fourth position opposite the third position, and, based on the third electric field and the fourth electric field, the simulated electric field distribution may be determined.

At 2040, determining, for each pair of positions of the plurality of pairs positions on the modified plane, a simulated electric field distribution. For example, At 2050, determining, based on the simulated electric field distributions, a dose metric for each pair of positions of the plurality of pairs positions.

At 2060, determining one or more sets of pairs of positions of the plurality of pairs of positions that satisfy an angular restriction between pairs of transducer arrays. For example, the angular restriction may be and/or indicate an orthogonal angle between the plurality of pairs of transducer arrays. The angular restriction, for example, may be and/or indicate a range of an angle between the plurality of pairs of transducer arrays.

At 2070, determining, based on the dose metrics and the one or more sets of pairs of positions that satisfy the angular restriction, one or more candidate transducer array layout maps.

In some instances, the method 2000 may comprise adjusting a simulated orientation or a simulated position for at least one transducer array at least one position of the one or more candidate transducer array layout maps, and determining, based on adjusting the simulated orientation or the simulated position for the at least one transducer array, a final transducer array layout map.

Figure 21:
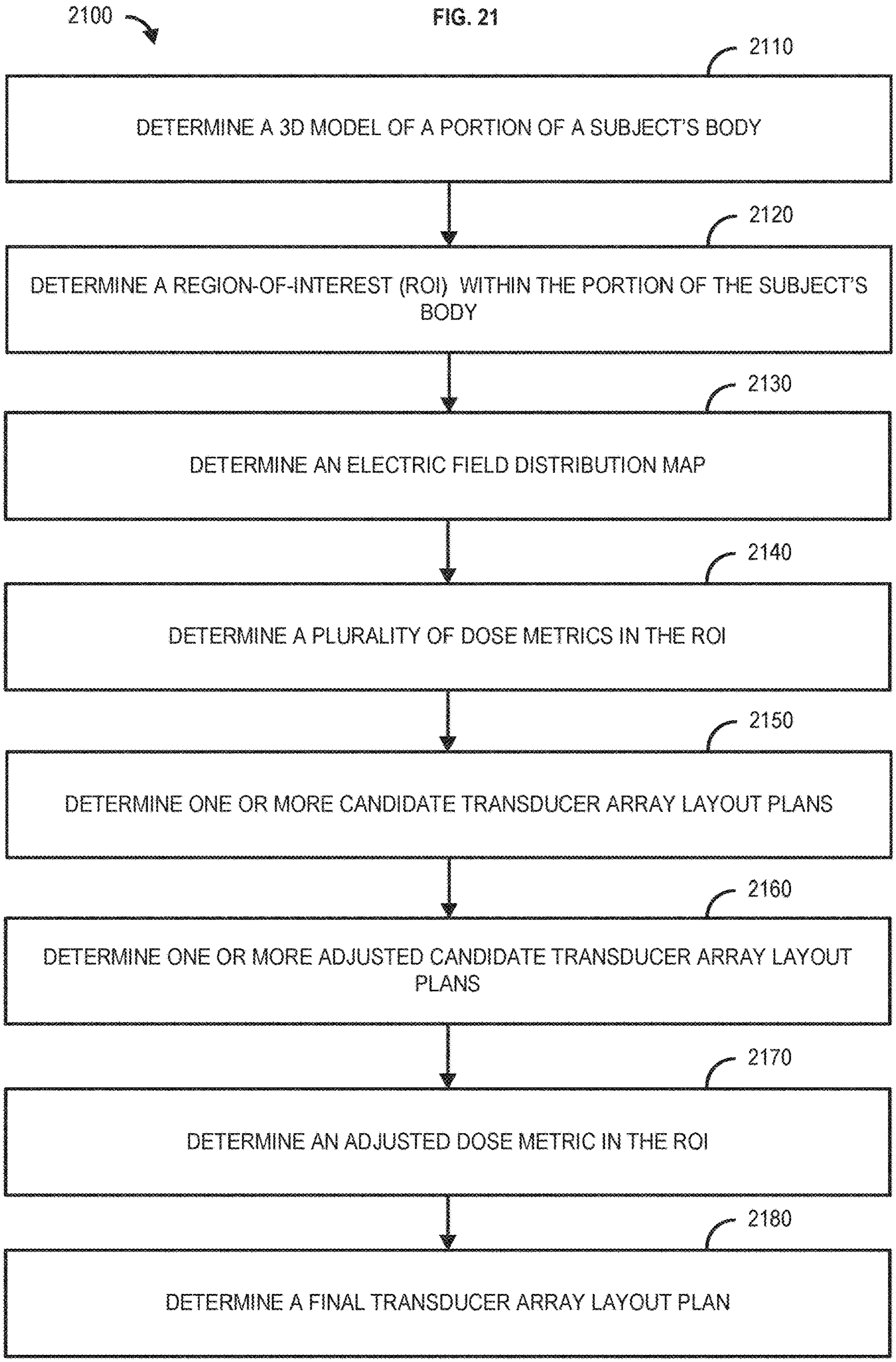
FIG. 21 shows an example method.

In an embodiment, illustrated in FIG. 21, one or more of the apparatus 100, the patient support system 602, the patient modeling application 608, and/any other device/component described herein can be configured to perform a method 2100 comprising, at 2110, determining a three-dimensional (3D) model of a portion of a subject's body.

At 2120, determining a region-of-interest (ROI) within the 3D model of the portion of the subject's body.

At 2130, determining, for each of a plurality of positions for a pair of transducer arrays, based on the 3D model, the ROI, and an anatomical restriction parameter, an electric field distribution map. The anatomical restriction parameter may indicate one or more positions of a transverse plane of the ROI that should be excluded from use in determining the electric field distribution map. In some instances, the method 2100 may comprise determining, based on a center of the ROI, a plane that transverses the portion of the subject's body, wherein the plane comprises the plurality of pairs of positions for the pair of transducer arrays along a contour of the plane, and adjusting, based on the anatomical restriction parameter, one or more positions of the plurality of pairs of positions to generate a modified plane.

At 2140, determining, for each combination of a plurality of combinations of two pairs of transducer arrays, based on the electric field distribution map, a plurality of dose metrics in the ROI. The plurality of dose metrics may be based on a simulated electric field generated for each combination of the plurality of combinations of two pairs of transducer arrays.

At 2150, determining, based on an angular restriction parameter and the plurality of dose metrics in the ROI, one or more candidate transducer array layout plans. In some instances, the angular restriction parameter may indicate an orthogonal angle between the plurality of pairs of transducer arrays. In some instances, the angular restriction parameter indicates a range of an angle between the plurality of pairs of transducer arrays.

At 2160, determining, for each of the one or more candidate transducer array layout plans, one or more adjusted candidate transducer array layout plans by adjusting a position or an orientation of one or more transducer arrays of the pair of transducer arrays.

At 2170, determining, for each adjusted candidate transducer array layout plan, an adjusted dose metric in the ROI.

At 2180, determining, based on the adjusted dose metric in the ROI, a final transducer array layout plan from the adjusted candidate transducer array layout plans.

In view of the described apparatuses, systems, and methods and variations thereof, herein below are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1: A method comprising: determining a region-of-interest (ROI) within a 3D model of a portion of a subject's body, determining, based on a center of the ROI, a plane that transverses the portion of the subject's body, wherein the plane comprises a plurality of pairs of positions along a contour of the plane, adjusting, based on an anatomical restriction, one or more positions of the plurality of pairs of positions to generate a modified plane, determining, for each pair of positions of the plurality of pairs positions on the modified plane, a simulated electric field distribution, determining, based on the simulated electric field distributions, a dose metric for each pair of positions of the plurality of pairs positions, determining one or more sets of pairs of positions of the plurality of pairs of positions that satisfy an angular restriction between pairs of transducer arrays, and determining, based on the dose metrics and the one or more sets of pairs of positions that satisfy the angular restriction, one or more candidate transducer array layout maps.

Embodiment 2: The embodiment as in any one of the preceding embodiments further comprising: adjusting a simulated orientation or a simulated position for at least one transducer array at at least one position of the one or more candidate transducer array layout maps, and determining, based on adjusting the simulated orientation or the simulated position for the at least one transducer array, a final transducer array layout map.

Embodiment 3: The embodiment as in any one of the preceding embodiments, wherein the anatomical restriction comprises an anatomical feature of the portion of the subject's body.

Embodiment 4: The embodiment as in any one of the preceding embodiments, wherein the angular restriction comprises an orthogonal angle between the plurality of pairs of transducer arrays.

Embodiment 5: The embodiment as in any one of the preceding embodiments, wherein the angular restriction comprises a range of an angle between the plurality of pairs of transducer arrays.

Embodiment 6: The embodiment as in any one of the preceding embodiments, wherein determining, for each pair of positions of the plurality of pairs positions on the modified plane, the simulated electric field distribution comprises: simulating, at a first position, a first electric field generated by a first transducer array, simulating, at a second position opposite the first position, a second electric field generated by a second transducer array, and determining, based on the first electric field and the second electric field, the simulated electric field distribution.

Embodiment 7: The embodiment as in any one of the preceding embodiments further comprising: simulating, at a third position, a third electric field generated by the first transducer array, simulating, at a fourth position opposite the third position, a fourth electric field generated by the second transducer array, and determining, based on the third electric field and the fourth electric field, the simulated electric field distribution.

Embodiment 8: The embodiment as in any one of the preceding embodiments determining, based on the combinations of the plurality of pairs of transducer arrays, the transducer array layout plan comprises: determining, for each of the one or more candidate transducer array layout plans, one or more adjusted candidate transducer array layout plans by adjusting a position or an orientation of one or more transducer arrays of the first pair of transducer arrays or one or more transducer arrays of the second pair of transducer arrays, determining, for each adjusted candidate transducer array layout plan an adjusted dose metric in the ROI, and determining, based on the adjusted dose metric in the ROI, a final transducer array layout plan from the adjusted candidate transducer array layout plans.

Embodiment 9: An apparatus, comprising: one or more processors; and memory storing processor-executable instructions that, when executed by the one or more processors, cause the apparatus to perform the methods of any embodiment as in any one of the embodiments 1-8.

Embodiment 10: One or more non-transitory computer-readable media storing processor-executable instructions thereon that, when executed by a processor, cause the processor to perform the methods of any embodiment as in any one of the embodiments 1-8.

Embodiment 11: A method comprising: determining a three-dimensional (3D) model of a portion of a subject's body, determining a region-of-interest (ROI) within the 3D model of the portion of the subject's body, determining, for each of a plurality of positions for a pair of transducer arrays, based on the 3D model, the ROI, and an anatomical restriction parameter, an electric field distribution map, determining, for each combination of a plurality of combinations of two pairs of transducer arrays, based on the electric field distribution map, a plurality of dose metrics in the ROI, determining, based on an angular restriction parameter and the plurality of dose metrics in the ROI, one or more candidate transducer array layout plans, determining, for each of the one or more candidate transducer array layout plans, one or more adjusted candidate transducer array layout plans by adjusting a position or an orientation of one or more transducer arrays of the pair of transducer arrays, determining, for each adjusted candidate transducer array layout plan, an adjusted dose metric in the ROI, and determining, based on the adjusted dose metric in the ROI, a final transducer array layout plan from the adjusted candidate transducer array layout plans.

Embodiment 12: The embodiment as in embodiment 11, further comprising adjusting a simulated orientation or a simulated position for at least one transducer array at at least one position of the one or more candidate transducer array layout maps, and determining, based on adjusting the simulated orientation or the simulated position for the at least one transducer array, a final transducer array layout map.

Embodiment 13: The embodiment as in any one of the embodiments 11-12, wherein the anatomical restriction parameter indicates one or more positions of a transverse plane of the ROI that should be excluded from use in determining the electric field distribution map.

Embodiment 14: The embodiment as in any one of the embodiments 11-13, wherein the angular restriction parameter indicates an orthogonal angle between the plurality of pairs of transducer arrays.

Embodiment 15: The embodiment as in any one of the embodiments 11-14, wherein the angular restriction parameter indicates a range of an angle between the plurality of pairs of transducer arrays.

Embodiment 16: The embodiment as in any one of the embodiments 11-15, further comprising: determining, based on a center of the ROI, a plane that transverses the portion of the subject's body, wherein the plane comprises the plurality of pairs of positions for the pair of transducer arrays along a contour of the plane, and adjusting, based on the anatomical restriction parameter, one or more positions of the plurality of pairs of positions to generate a modified plane.

Embodiment 17: The embodiment as in any one of the embodiments 11-16, wherein the plurality of dose metrics are based on a simulated electric field generated for each combination of the plurality of combinations of two pairs of transducer arrays.

Embodiment 18: An apparatus, comprising: one or more processors; and memory storing processor-executable instructions that, when executed by the one or more processors, cause the apparatus to perform the methods of any embodiment as in any one of the embodiments 11-17.

Embodiment 19: One or more non-transitory computer-readable media storing processor-executable instructions thereon that, when executed by a processor, cause the processor to perform the methods of any embodiment as in any one of the embodiments 11-17.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A computer-implemented method for determining a transducer array layout plan, comprising:

determining, by one or more processors, a three-dimensional (3D) model of a portion of a subject's body;

determining, by the one or more processors, a region-of-interest (ROI) within the 3D model of the portion of the subject's body;

determining, by the one or more processors and for each of a plurality of positions for a pair of transducer arrays, based on the 3D model, the ROI, and an anatomical restriction parameter, an electric field distribution map;

determining, by the one or more processors and for each combination of a plurality of combinations of two pairs of transducer arrays, based on the electric field distribution map, a plurality of dose metrics in the ROI;

determining, by the one or more processors and based on an angular restriction parameter and the plurality of dose metrics in the ROI, one or more candidate transducer array layout plans;

determining, by the one or more processors and for each of the one or more candidate transducer array layout plans, one or more adjusted candidate transducer array layout plans by adjusting a position or an orientation of one or more transducer arrays of the pair of transducer arrays;

determining, by the one or more processors and for each adjusted candidate transducer array layout plan, an adjusted dose metric in the ROI; and determining, by the one or more processors and based on the adjusted dose metric in the ROI, the transducer array layout plan from the adjusted candidate transducer array layout plans.

2. The method of claim 1, wherein the anatomical restriction parameter indicates one or more positions of a transverse plane of the ROI that should be excluded from use in determining the electric field distribution map.

3. The method of claim 1, wherein the angular restriction parameter indicates an orthogonal angle between the plurality of pairs of transducer arrays.

4. The method of claim 1, wherein the angular restriction parameter indicates a range of an angle between the plurality of pairs of transducer arrays.

5. The method of 1, further comprising:

determining, by the one or more processors and based on a center of the ROI, a plane that transverses the portion of the subject's body, wherein the plane comprises the plurality of pairs of positions for the pair of transducer arrays along a contour of the plane; and adjusting, by the one or more processors and based on the anatomical restriction parameter, one or more positions of the plurality of pairs of positions to generate a modified plane.

6. The method of 1, wherein the plurality of dose metrics are based on a simulated electric field generated for each combination of the plurality of combinations of two pairs of transducer arrays.

7. The method of claim 1, further comprising:

adjusting, by the one or more processers, a simulated orientation or a simulated position for at least one transducer array of the one or more candidate transducer array layout maps, wherein the transducer array layout plan is further determined based on adjusting the simulated orientation or the simulated position for the at least one transducer array.

8. An apparatus for determining a transducer array layout plan, comprising:

one or more processors; and memory storing processor-executable instructions that, when executed by the one or more processors, cause the apparatus to:

determine a three-dimensional (3D) model of a portion of a subject's body;

determine a region-of-interest (ROI) within the 3D model of the portion of the subject's body;

determine, for each of a plurality of positions for a pair of transducer arrays, based on the 3D model, the ROI, and an anatomical restriction parameter, an electric field distribution map;

determine, for each combination of a plurality of combinations of two pairs of transducer arrays, based on the electric field distribution map, a plurality of dose metrics in the ROI;

determine, based on an angular restriction parameter and the plurality of dose metrics in the ROI, one or more candidate transducer array layout plans;

determine, for each of the one or more candidate transducer array layout plans, one or more adjusted candidate transducer array layout plans by adjusting a position or an orientation of one or more transducer arrays of the pair of transducer arrays;

determine, for each adjusted candidate transducer array layout plan, an adjusted dose metric in the ROI; and determine, based on the adjusted dose metric in the ROI, the transducer array layout plan from the adjusted candidate transducer array layout plans.

9. The apparatus of claim 8, wherein the anatomical restriction parameter indicates one or more positions of a transverse plane of the ROI that should be excluded from use in determining the electric field distribution map.

10. The apparatus of claim 8, wherein the angular restriction parameter indicates an orthogonal angle between the plurality of pairs of transducer arrays.

11. The apparatus of claim 8, wherein the angular restriction parameter indicates a range of an angle between the plurality of pairs of transducer arrays.

12. The apparatus of claim 8, wherein the processor executable instructions, when executed by the one or more processors, further cause the apparatus to:

determine, based on a center of the ROI, a plane that transverses the portion of the subject's body, wherein the plane comprises the plurality of pairs of positions for the pair of transducer arrays along a contour of the plane; and adjust, based on the anatomical restriction parameter, one or more positions of the plurality of pairs of positions to generate a modified plane.

13. The apparatus of claim 8, wherein the plurality of dose metrics are based on a simulated electric field generated for each combination of the plurality of combinations of two pairs of transducer arrays.

14. The apparatus of claim 8, wherein the processor executable instructions, when executed by the one or more processors, further cause the apparatus to:

adjust a simulated orientation or a simulated position for at least one transducer array of the one or more candidate transducer array layout maps, wherein the transducer array layout plan is further determined based on adjusting the simulated orientation or the simulated position for the at least one transducer array.

15. A non-transitory computer-readable storage medium storing processor-executable instructions for determining a transducer array layout plan that, when executed by one or more processors, cause the one or more processors to perform operations comprising:

determining a three-dimensional (3D) model of a portion of a subject's body;

determining a region-of-interest (ROI) within the 3D model of the portion of the subject's body;

determining, for each of a plurality of positions for a pair of transducer arrays, based on the 3D model, the ROI, and an anatomical restriction parameter, an electric field distribution map;

determining, for each combination of a plurality of combinations of two pairs of transducer arrays, based on the electric field distribution map, a plurality of dose metrics in the ROI;

determining, based on an angular restriction parameter and the plurality of dose metrics in the ROI, one or more candidate transducer array layout plans;

determining, for each of the one or more candidate transducer array layout plans, one or more adjusted candidate transducer array layout plans by adjusting a position or an orientation of one or more transducer arrays of the pair of transducer arrays;

determining, for each adjusted candidate transducer array layout plan, an adjusted dose metric in the ROI; and determining, based on the adjusted dose metric in the ROI, the transducer array layout plan from the adjusted candidate transducer array layout plans.

16. The non-transitory computer-readable storage medium of claim 15, wherein the anatomical restriction parameter indicates one or more positions of a transverse plane of the ROI that should be excluded from use in determining the electric field distribution map.

17. The non-transitory computer-readable storage medium of claim 15, wherein the angular restriction parameter indicates an orthogonal angle between the plurality of pairs of transducer arrays.

18. The non-transitory computer-readable storage medium of claim 15, wherein the angular restriction parameter indicates a range of an angle between the plurality of pairs of transducer arrays.

19. The non-transitory computer-readable storage medium of 15, further configuring the one or more processors to perform operations comprising:

determining, based on a center of the ROI, a plane that transverses the portion of the subject's body, wherein the plane comprises the plurality of pairs of positions for the pair of transducer arrays along a contour of the plane; and adjusting, based on the anatomical restriction parameter, one or more positions of the plurality of pairs of positions to generate a modified plane.

20. The non-transitory computer-readable storage medium of 15, wherein the plurality of dose metrics are based on a simulated electric field generated for each combination of the plurality of combinations of two pairs of transducer arrays.

* * * * *